United States Patent
Xue et al.

(10) Patent No.: US 11,903,948 B2
(45) Date of Patent: Feb. 20, 2024

(54) ANTI-ERBB2 ANTIBODY-DRUG CONJUGATE AND COMPOSITION THEREOF, PREPARATION METHOD THEREFOR, AND USE THEREOF

(71) Applicant: SICHUAN KELUN-BIOTECH BIOPHARMACEUTICAL CO., LTD., Sichuan (CN)

(72) Inventors: Tongtong Xue, Sichuan (CN); Zhenwei Miao, San Diego, CA (US); Jing Wang, Sichuan (CN); Gang Chen, San Diego, CA (US); Yan Qing, Sichuan (CN); Tong Zhu, San Diego, CA (US); Liang Xiao, Sichuan (CN); Hong Zhang, San Diego, CA (US); Qiuyan Yang, Sichuan (CN); Dylan Dalun Deng, San Diego, CA (US); Liping Liu, Sichuan (CN); Hong Zeng, Sichuan (CN); Li Yin, Sichuan (CN); Qifeng Shi, Sichuan (CN); Hongmei Song, Sichuan (CN); Xi Zhao, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 25 days.

(21) Appl. No.: 17/169,087

(22) Filed: Feb. 5, 2021

(65) Prior Publication Data
US 2021/0252006 A1    Aug. 19, 2021

Related U.S. Application Data

(62) Division of application No. 15/765,685, filed on Apr. 3, 2018.

(30) Foreign Application Priority Data

Nov. 23, 2015    (CN) .......................... 201510824064.8

(51) Int. Cl.
A61K 31/536    (2006.01)
A61K 47/68    (2017.01)
(Continued)

(52) U.S. Cl.
CPC ............ *A61K 31/536* (2013.01); *A61K 47/64* (2017.08); *A61K 47/65* (2017.08);
(Continued)

(58) Field of Classification Search
None
See application file for complete search history.

(56) References Cited

U.S. PATENT DOCUMENTS 5,821,337 A    10/1998    Carter et al.
8,741,291 B2    6/2014    Bhat et al.
(Continued)

FOREIGN PATENT DOCUMENTS

CN    1938046 A    3/2007
CN    102973947 A    3/2013
(Continued)

OTHER PUBLICATIONS

Zhang et al., Tetrahedron Letters 50 (2009) 2964-2966 (Year: 2009).*
(Continued)

*Primary Examiner* — Karl J Puttlitz
(74) *Attorney, Agent, or Firm* — Rothwell, Figg, Ernst & Manbeck, P.C.

(57) ABSTRACT

Provided is a preparation method of an antibody-drug conjugate represented by Formula (I), or a pharmaceutically
(Continued)

acceptable salt or stereoisomer thereof, or a solvate of the foregoing,

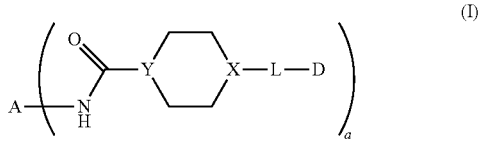

wherein A, X, Y, L, D and a are as defined herein.

7 Claims, 11 Drawing Sheets

Specification includes a Sequence Listing.

(51) Int. Cl.
    A61K 47/65    (2017.01)
    A61K 47/64    (2017.01)
    A61P 35/00    (2006.01)
    C07K 16/32    (2006.01)
(52) U.S. Cl.
    CPC ...... *A61K 47/6803* (2017.08); *A61K 47/6869* (2017.08); *A61P 35/00* (2018.01); *C07K 16/32* (2013.01); *C07K 2317/24* (2013.01)

(56) References Cited

U.S. PATENT DOCUMENTS

| | | | |
|---|---|---|---|
| 10,590,165 B2* | 3/2020 | Miao | A61P 35/00 |
| 2005/0232929 A1 | 10/2005 | Kadkhodayan et al. | |
| 2015/0105540 A1 | 4/2015 | Miao et al. | |
| 2019/0076438 A1 | 3/2019 | Xue et al. | |
| 2019/0091345 A1 | 3/2019 | Miao et al. | |

FOREIGN PATENT DOCUMENTS

| | | | |
|---|---|---|---|
| CN | 103269712 A | | 8/2013 |
| CN | 103319599 A | | 9/2013 |
| CN | 104640572 A | | 5/2015 |
| CN | 104888231 A | | 9/2015 |
| CN | 104892763 A | | 9/2015 |
| CN | 105051032 A | | 11/2015 |
| CN | 107915770 | * | 4/2018 |
| CN | 107921124 A | | 4/2018 |
| EP | 3412315 A1 | | 12/2018 |
| JP | 2012207036 A2 | | 10/2012 |
| JP | 2013163687 A2 | | 8/2013 |
| JP | 2013224305 A | | 10/2013 |
| JP | 6888871 B2 | | 6/2021 |
| WO | 2005081711 A2 | | 9/2005 |
| WO | 2005117986 A2 | | 12/2005 |
| WO | 2009117277 A2 | | 9/2009 |
| WO | 2013173392 | * | 11/2013 |
| WO | 2013173392 A1 | | 11/2013 |
| WO | 2013173393 A1 | | 11/2013 |
| WO | 20130173391 A1 | | 11/2013 |
| WO | 2015047510 A1 | | 4/2015 |
| WO | 20150104385 A2 | | 7/2015 |
| WO | 2016123412 | * | 8/2016 |
| WO | 2016123412 A1 | | 8/2016 |
| WO | 2018036438 | * | 3/2018 |

OTHER PUBLICATIONS

Eurasian Office Action issued in corresponding EA Application No. 201792590/28, dated Apr. 1, 2020, 6 pages, with English translation.
International Search Report and Written Opinion issued in Application No. PCT/CN2016/106802 dated Feb. 21, 2017, 16 pages.
Lazar C. A. et al., "Analysis of the composition of immunoconjugates using size-exclusion chromatography coupled to mass spectrometry", Rapid Communications in Mass Spectrometry, 2005(19), p. 1806-1814.
Chinese Office Action issued in Application No. 201680036760.5 dated Aug. 17, 2018, 16 pages.
Zhu, Gui-dong et al., "Design of next generation antibody drug conjugates", Acta Pharmaceutica Sinica 2013, 48(7): pp. 1053-1070.
Goldmacher, Victor S., "Antibody-Drug Conjugates for Targeted Cancer Therapy", Annual Reports in Medicinal Chemistry, vol. 47, Chapter 23, 2012, 18 pages.
Yao, Y., et al., "Synthesis, characterization and targeting chemotherapy for ovarian cancer of trastuzumab-SN-38 conjugates" Journal of Controlled Release, Elsevier, Amsterdam, NL, vol. 220, Oct. 9, 2015, pp. 5-17.
Altai, M., et al., "Affibody-derived drug conjugates: Potent cytotoxic molecules for treatment of HER2 over-expressing tumors" Journal of Controlled Release, Elsevier, Amsterdam, NL, vol. 288, Aug. 30, 2018, pp. 84-95.
Rinnerthaler, G., et al., "HER2 Directed Antibody-Drug-Conjugates beyond T-DM1 in Breast Cancer" International Journal of Molecular Sciences vol. 20 No. 1115, Mar. 5, 2019, pp. 1-17.
Extended European Search Report issued for European Patent Application No. 16867957.9 dated Jul. 1, 2019, 8 pages.
Communication pursuant to Article 94(3) EPC dated Apr. 2, 2020 issued in European Patent Application No. 16867 957.9 (5 pages).
Communication pursuant to Article 94(3) EPC in European patent application No. 16 867 957.9 dated Aug. 3, 2020, 5 pages.
International Search Report issued in corresponding Chinese Application No. 201510824064.8, dated Sep. 22, 2020, (5 pages).
Communication issued in corresponding Japanese Application No. 2017-566133, dated Oct. 8, 2020, (10 pages).
Chinese Second Office Action issued in corresponding Application No. 201510824064.8, dated Jun. 9, 2021, 8 pages (with English Translation).
Chinese First Office Action issued in corresponding Application No. 201811298547.9, dated Jun. 9, 2021, 23 pages (with English Translation).
Chinese First Office Action issued in corresponding Application No. 201811298611.3, dated Jun. 24, 2021, 13 pages (with English Translation).
Office Action issued for Japanese Patent Application No. 2021-083093 dated May 31, 2022 with English translation, 3 pages.
Non-Final Office Action issued for U.S. Appl. No. 15/765,685 dated Jun. 28, 2022, 22 pages.
Office Action issued in corresponding U.S. Appl. No. 15/765,685, dated Jul. 12, 2021, 35 pages.
Behrens, Mabs, Jan. 1, 2014, 6(1):46-53 (Year: 2014), 9 pages.
Database Caplus Chemical Abstracts Service, Columbus, Ohio, US; Database Accession No. 2018:759324, Abstract of CN 107915770, Levena (Suzhou) Biopharma Co., Ltd., Peop. Rep. China, Khasanov et al., Oct. 11, 2016 (Year: 2016), 5 pages.
Second Chinese Office Action dated Jan. 28, 2022, issued in Chinese Patent Application No. 201811298547.9, 21 pages.
Final Office Action issued for U.S. Appl. No. 15/765,685 dated Mar. 28, 2022, 31 pages.
Bhat et al. "The Next Step in Homogenous Bioconjugate Development: Optimizing Payload Placement and Conjugate Composition" downloaded Mar. 23, 2022 from https://bioprocessintl.com/manufacturing/monoclonal-antibodies/next-step-homogenous-bioconjugate-development-optimizing-payload-placement-conjugate-co (2014), 12 pages.
Canadian Office Action issued in Canadian Application No. 3,000,763, dated Dec. 1, 2022, 7 pages.
Non-Final Office Action dated Sep. 7, 2023 in corresponding U.S. Appl. No. 15/765,685, First Named Inventor Tongtong Xue (17 pages).
Panowski et al., mAbs, 2014, 6:1, 34-45 (Year: 2014) (13 pages).

* cited by examiner

SEQUENCE LISTING

<160> NUMBER OF SEQ ID NOS: 2

<210> SEQ ID NO 1
<211> LENGTH: 450
<212> TYPE: PRT
<213> ORGANISM: Artificial Sequence

```
<220> FEATURE:
<223> OTHER INFORMATION: humanized murine antibody heavy chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: humanized murine antibody light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

ANTI-ERBB2 ANTIBODY-DRUG CONJUGATE AND COMPOSITION THEREOF, PREPARATION METHOD THEREFOR, AND USE THEREOF

CROSS REFERENCE TO RELATED APPLICATIONS

This application is a divisional of U.S. application Ser. No. 15/765,685, filed Apr. 3, 2018, which application is a National Phase Entry of PCT/CN2016/106802, filed Nov. 22, 2016, which claims priority to CN 201510824064.8, filed Nov. 23, 2015, the teachings of which are hereby incorporated by reference in their entireties for all purposes.

FIELD OF THE INVENTION

The present invention pertains to the field of biomedical technology. In particular, the present invention relates to anti-ErbB2 antibody-drug conjugates, compositions comprising the same, and preparation methods and uses thereof.

BACKGROUND OF THE INVENTION

Antibody-drug conjugates (ADCs), as novel medicines for targeted therapy, usher in a new era of cancer therapy. With Seattle Genetics, Inc. and ImmunoGen, Inc in the lead, many multinational pharmaceutical enterprises and start-ups are involved in the research and development in this field. According to a report from Market Research, there are currently a total of 45 ADCs in clinical trials worldwide.

An ADC typically includes three moieties, antibody, linker(s) and drug(s), which are connected in a certain way.

Antibodies are good targeting carriers for drugs. A drug and an antibody can be conjugated through a specific functional group, such as hydroxyl, mercapto or amino, to form a chemoimmunoconjugate. Drugs conjugated to antibodies can be transported to target cells precisely due to the targeting capability of the antibodies, thereby effectively increasing local drug concentration at the disease site while greatly lowering drug concentration in other tissues or organs to achieve increased efficacy and reduced toxicity. The polyclonal and monoclonal antibodies used in these strategies have been reported (Rowland et al., 1986, Cancer Immunol. Immunother., 21: 183-87). The antibodies in the ADCs clinically used at present are mostly humanized antibodies, e.g., those in PSMA ADC (anti-PSMA antibody-MMAE conjugate), SGN-75 (anti-CD70 antibody-MMAF conjugate) and T-DM1 (Trastuzumab-DM1 conjugate) are all humanized antibodies. So far, FDA-approved ADCs include Kadcyla® (T-DM1) and Adcetris® (brentuximab vedotin).

The drugs as "warheads" in ADCs are usually cytotoxic agents, which kill tumor cells mainly by inhibiting DNA or protein synthesis in the cells, inhibiting cell mitosis, and the like. Because cytotoxic agents are also lethal to normal cells, their development and application are greatly limited. Early ADCs use conventional antineoplastic agents, but their clinical activity is generally lower than the activity of the agents in vitro. The cytotoxic agents in current ADCs include: Maytansinoids (see e.g., EP 0425235, U.S. Pat. Nos. 5,208,020, 5,416,064, 7,276,497, 7,473,796, 7,851,432, US 2007/0269447, US 2011/0158991, WO 2004/103272, WO 2012/061590), Auristatins (see e.g., U.S. Pat. Nos. 6,884,869, 7,498,298), Calicheamicins (see e.g., U.S. Pat. Nos. 5,606,040, 5,770,710), Doxorubicins (see e.g., Dubowchik et al., 2002, Bioconjugate Chem., 13: 855-869), Duocarmycins and CC-1065 (see e.g., U.S. Pat. No. 7,129,261), Irinotecan metabolites (see e.g., WO 2015/012904), pyrrolobenzodiazepines (see e.g., Biotechnol. Healthc. 2012 Winter, 9 (4): 28-31) and pyrrolobenzodiazepine dimmers (PBD dimmers, see e.g., WO 2005/040170). These cytotoxic agents have very strong non-selective toxicity, will damage normal cells, and thus cannot be used as medicines per se.

Linkers in ADCs must satisfy the requirements of preventing detachment of small-molecular drugs from antibodies outside cells, and upon internalization into cells, for cleavable linkers, cleaving under appropriate conditions to release active small-molecular drugs, while for non-cleavable linkers, forming active moiety together with small-molecular drugs and amino acid residues resulting from enzymatic hydrolysis of the antibodies.

In the ADCs currently in clinical trials, cytotoxic agents are generally linked, via linkers, to the lysine residues on antibody surface or to the cysteine residues in antibody hinge region (available after partial reduction of interchain disulfide bonds). When the agents are linked to the lysine residues on antibody surface, since a large number of lysine residues (over 80 lysine residues) exist on the antibody surface and the conjugation reaction is non-selective, there is uncertainty in terms of conjugation sites and conjugated agent numbers, leading to heterogeneity of the resulting ADCs. For example, T-DM1 has a DAR (drug antibody ratio) value distribution of 0-8, and an average DAR of 3.5 (Lazar et al., 2005, Rapid Commun. Mass Spectrom., 19: 1806-1814). Typically, ADCs have a DAR in the range of 2-4. When the agents are linked to the cysteine residues in antibody hinge region, since only four inter-chain disulfide bonds exist in the hinge region, it is necessary to partially reduce the interchain disulfide bonds (Sun et al., 2005, Bioconjugate Chem., 16: 1282-1290). Current reducing agents such as dithiothreitol (DTT) and trichloroethyl phosphate (TCEP), however, cannot selectively reduce the interchain disulfide bonds, and in turn the ADCs thus obtained are not homogeneous products, but mixtures of multiple components wherein the DAR of the primary components are 0, 2, 4, 6 and 8 and for each DAR value, there are different isomers resulting from different conjugation sites. The heterogeneity of ADC products is disadvantageous to the clinical application thereof due to different pharmacokinetics, potency, and toxicity of different components in the products (for example, components with higher DAR are cleared more rapidly in vivo and contribute to more severe toxicity, see Boswell et al., 2011, Bioconjugate Chem., 22: 1994-2004), rendering unsatisfactory stability.

ErbB receptor tyrosine kinase family is an important regulator for cell growth, differentiation and survival. The family includes four members: epithelial growth factor receptor (EGFR or ErbB1), Her2 (ErbB2), Her3 (ErbB3) and Her4 (ErbB4).

The anti-ErbB2 antibody, Trastuzumab, has been used clinically for the treatment of ErbB2-overexpressing breast cancer. In a clinical trial, 15% of the patients with immunohistochemistry (IHC) levels above 2+ had a clinical response to Trastuzumab, and the median response was 9.1 months (see e.g., Cobleigh et al., 1996, Journal of Clinical Oncology, 14: 737-744). Trastuzumab (Herceptin) was approved by the US Food and Drug Administration (FDA) on Sep. 25, 1998 for the treatment of patients suffering from ErbB2-overexpressing breast cancer.

Although Trastuzumab has saved some breast cancer patients or prolonged patients' survival, it is only effective in ErbB2-overexpressing patients, and the clinical response rate is only 15%. Therefore, there remains a need for medicines with better efficacy for more patients.

Trastuzumab has been conjugated with maytansine (DM1) to form Trastuzumab emtansine (T-DM1, Kadcyla®) in order to improve therapeutic index. T-DM1 is used in patients to whom treatments with Trastuzumab, first-line taxanes and other anti-Her2 therapeutic agents are ineffective. T-DM1 delivers drugs to tumors to reduce tumor size, delay disease progression, and prolong survival. In clinical trials, the safety and efficacy of T-DM1 were evaluated. T-DM1 has become the fourth medicine targeting Her2 approved by FDA. However, there was a black box warning for T-DM1 when it was approved, reminding patients and health care professionals that T-DM1 may lead to hepatotoxicity, cardiotoxicity and death. This is mainly due to detached DM1 and DM1-containing small molecules released upon degradation of T-DM1 in vivo.

T-DM1 is prepared by coupling the lysine side chain amino group on Trastuzumab with sulfosuccinimidyl 4-[N-maleimidomethyl]cyclohexane-1-carboxylate (sulfo-SMCC), and then conjugating DM1. On average, 3.5 DM1 molecules are conjugated to one Trastuzumab molecule in T-DM1. Since there are 88 lysine residues on Trastuzumab, T-DM1 is actually a combination of various ADCs in which different number of DM1 molecules are conjugated and which have a variety of coupling sites. However, the efficacy, pharmacokinetics and/or toxicity differ among the ADCs. In general, high drug-loading ADCs have higher in vitro activity, though high drug loading also cause a number of problems, such as increased amounts of polymers due to aggregation of ADCs, decreased stability, increased toxicity, increased immunogenicity, rapid in vivo clearance rate, decreased half-life and poor therapeutic index.

The present invention aims at solving the above problems in the prior art. The present invention provides anti-Her2 antibody-drug conjugates that inhibit tumor growth in mammals and can be used for treating a variety of cancers. The conjugates have better biological activity, stability, homogeneity, and reduced toxic side effects.

SUMMARY OF THE INVENTION

In a first aspect, the present invention provides an antibody-drug conjugate of Formula (I), or a pharmaceutically acceptable salt, stereoisomer or metabolite thereof, or a solvate of the foregoing,

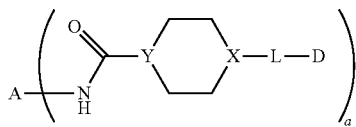

wherein:
A is an anti-ErbB2 antibody or an active fragment or variant thereof;
each of X and Y is independently N or $CR^1$, and $R^1$ at each occurrence is independently H or $C_1$-$C_{10}$alkyl;
L is a divalent linker;
D is a cytotoxic agent group; and
a is an integer selected from the group consisting of 2-10.

In a second aspect, the present invention provides a preparation method of the antibody-drug conjugate of the first aspect, comprising the steps of:

(1). preparing a compound of Formula (I-A)

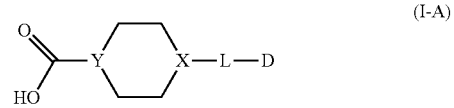

wherein D, L, X and Y are as defined in Formula (I) above;
(2). obtaining a compound of Formula (I-A-G) by activating the compound of Formula (I-A) from step (1)

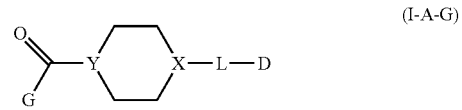

wherein G is selected from the group consisting of —F, —Cl, —Br, —I, —$N_3$, —OR, —SR, —ONRR', RC(O)O—, —OP(O)RR', $RSO_2$—O—, and

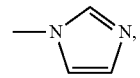

wherein each of R and R' at each occurrence is independently selected from the group consisting of $C_1$-$C_{10}$ alkyl, $C_6$-$C_{14}$ aryl, heterocyclyl having 5 to 10 ring members, or phenoxy, and each of the alkyl, aryl, heterocyclyl and phenoxy is unsubstituted or independently substituted with one or more substituents selected from the group consisting of halogen, hydroxy, $C_1$-$C_4$ alkyl, $C_1$-$C_4$ alkoxy, $C_3$-$C_8$ cycloalkyl, heterocyclyl having 5 to 8 ring members, $C_6$-$C_{10}$ aryl and heteroaryl having 5 to 10 ring members;

(3). obtaining a mixture of antibody-drug conjugates having different a values by conjugating the compound of Formula (I-A-G) from step (2) with an anti-ErbB2 antibody or an active fragment or variant thereof; and (4). obtaining the antibody-drug conjugate by purifying the mixture from step (3) with one or more chromatographic methods selected from the group consisting of ion exchange chromatography, hydrophobic chromatography, reverse phase chromatography and affinity chromatography.

In a third aspect, the present invention provides a pharmaceutical composition comprising the antibody-drug conjugate of the first aspect of the present invention or a pharmaceutically acceptable salt, stereoisomer or metabolite thereof, or a solvate of the foregoing, and a pharmaceutically acceptable carrier.

In a fourth aspect, the present invention provides use of the antibody-drug conjugate of the first aspect of the present invention or a pharmaceutically acceptable salt, stereoisomer or metabolite thereof, or a solvate of the foregoing in the manufacture of a medicament for the prophylaxis or treatment of cancer.

In a fifth aspect, the present invention provides a pharmaceutical preparation comprising the antibody-drug conjugate of the first aspect of the present invention or a pharmaceutically acceptable salt, stereoisomer or metabolite thereof, or a solvate of the foregoing.

In a sixth aspect, the present invention provides a method for the prophylaxis or treatment of cancer, comprising administering to a patient in need thereof the antibody-drug conjugate of the first aspect of the present invention, a pharmaceutically acceptable salt, stereoisomer or metabolite thereof, or a solvate of the foregoing, or administering to a patient in need thereof the pharmaceutical composition of the third aspect of the present invention or the pharmaceutical preparation of the fifth aspect of the present invention.

DETAILED DESCRIPTION OF THE INVENTION

Figure 1:
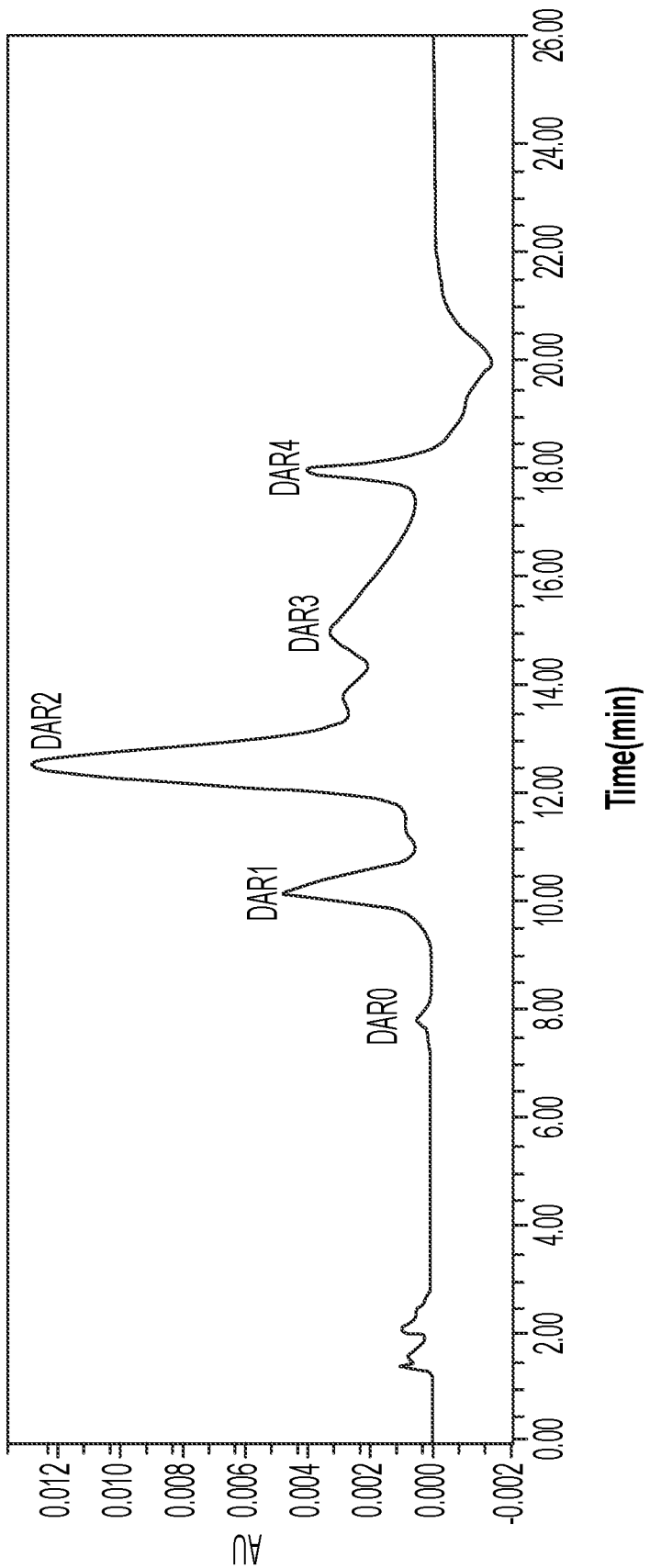
FIG. 1 shows a HIC-HPLC chromatogram of crude Antibody-Drug Conjugate I-1.

Unless otherwise defined, all the terms used herein have the same meaning as commonly understood by one of ordinary skill in the art. Relevant definitions and terms can be found in e.g., Current Protocols in Molecular Biology (Ausubel).

The numerical ranges described herein are to be understood as encompassing any and all sub-ranges subsumed therein. For example, the range "1 to 10" is to be understood as including not only the clearly stated values of 1 to 10 but also any single values in the range of 1 to 10 (e.g., 2, 3, 4, 5, 6, 7, 8, and 9) and sub-ranges (e.g., 1 to 2, 1.5 to 2.5, 1 to 3, 1.5 to 3.5, 2.5 to 4, 3 to 4.5, etc.). The principle also applies to a range where only one value is indicated as the minimum or maximum value.

All references mentioned throughout the specification are incorporated herein by reference in their entirety.

In the first aspect, the present invention provides an antibody-drug conjugate of Formula (I), or a pharmaceutically acceptable salt, stereoisomer or metabolite thereof, or a solvate of the foregoing,

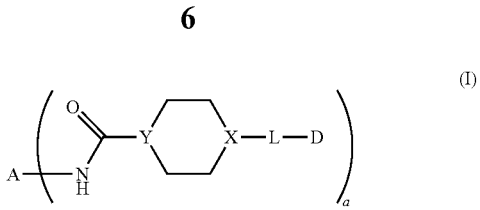

wherein:
A is an anti-ErbB2 antibody or an active fragment or variant thereof;
each of X and Y is independently N or $CR^1$ (preferably, Y is $CR^1$, and X is N), and $R^1$ at each occurrence is independently H or $C_1$-$C_{10}$alkyl, preferably H or $C_1$-$C_6$ alkyl (e.g., methyl, ethyl, n-propyl, isopropyl, n-butyl, isobutyl, t-butyl, pentyl or hexyl);
L is a divalent linker;
D is a cytotoxic agent group; and
a is an integer selected from the group consisting of 2-10, such as 2, 3 or 4, and particularly preferably 2.

Antibody

The antibodies used in the present invention are anti-ErbB2 antibodies or active fragments or variants thereof, including bispecific antibodies and antibody functional derivatives.

The terms "ErbB2" and "HER2" are used interchangeably herein, and both refer to naturally occurring human HER2 protein (Genbank accession number X03363, see e.g., Semba et al., (1985) PNAS, 82: 6497-6501; and Yamamoto et al., (1986) Nature, 319: 230-234), and functional derivatives thereof, e.g., amino acid sequence variants. The term "erbB2" refers to the gene encoding human Her2, and the term "neu" refers to the gene encoding rat p185neu. Cancer cells, such as breast cancer cells, ovarian cancer cells, stomach cancer cells, endometrial cancer cells, salivary-gland cancer cells, lung cancer cells, kidney cancer cells, colon cancer cells, thyroid cancer cells, pancreatic cancer cells, bladder cancer cells or liver cancer cells, etc., typically are cells expressing ErbB2 receptor.

The preferred Her2 in the present invention is a native sequence of human Her2. Examples of anti-Her2 antibodies that can be used in the present invention include, but are not limited to, MAbs4D5 (ATCC CRL 10463), 2C4 (ATCC HB-12697), 7F3 (ATCC HB-12216) and 7C2 (ATCC HB 12215), which are described in e.g., U.S. Pat. No. 5,772,997, WO 98/77797 and U.S. Pat. No. 5,840,525.

Humanized anti-Her2 antibodies include huMAb4D5, huMAb4D5-1, huMAb4D5-2, huMAb4D5-3, huMAb4D5-4, huMAb4D5-5, huMAb4D5-6, huMAb4D5-7 and huMAb4D5-8 described in Table 3 of U.S. Pat. No. 5,821,337; and 7C2, 7F3, 2C4, 7D3, 3E8 and 2C4 shown in FIG. 1B of CN 1370082A.

Examples of the anti-HER2 antibodies that can be used in the present invention can further include: F243L, R292P and Y300L; F243L, R292P and V305I; F243L, R292P and P396L; and R292P, V305I and P396 described in WO 2009/123894; MM-111 described in WO 2012/079093; antibody $TP_S$, $TP_L$, $PT_S$ or $PT_L$ described in claims 2 to 10 of CN 104418952A; antibody Dl, Dl.5, Dl.5-100, DLlI, DL1 Ib or DL1 If described in FIG. 33A and FIG. 33B of WO 2010/108127; and humanized 520C9 described in WO 93/21319.

The native sequence of Her2 in the present invention can be isolated from nature, or can be produced by recombinant DNA technology, chemical synthesis, or a combination thereof.

The term "functional derivative" includes amino acid sequence variants and native polypeptide covalent derivatives (e.g., those obtained by post-translational modification, pyroglutamic acid derivatization, and the like), provided that they retain affinity and biological activity that are comparable to or higher than those of the native polypeptide. Amino acid sequence variants and native polypeptide amino acid sequence generally differ in one or more amino acid substitutions, deletions and/or insertions in the latter. Deletion variants include fragments of the native polypeptide and the N-terminal and/or C-terminal truncated variants. Typically, amino acid sequence variants and the native polypeptide should have at least 70%, or at least 80%, or at least 90% homology. Native polypeptide covalent derivatives can be those obtained by changing the post-translational processing of an antibody, for example, changing the number or location of glycosylation sites.

The terms "homology", "consistency", "identity" and "similarity" are used interchangeably herein, and refer to a percentage of identical nucleotides or of identical amino acid residues between two nucleic acid or amino acid sequences to be compared, obtained after the best alignment (optimum alignment), this percentage being purely statistical and the differences between the two sequences being distributed randomly and over their entire length. The alignment between two nucleic acid or amino acid sequences is typically carried out by comparing these sequences after having aligned them in an optimum manner, and the comparison can be carried out by segment or by "comparison window". An optimum alignment can be carried out, in addition to manually, by other methods described in references, e.g., the local homology algorithm described in Smith and Waterman, 1981, Ad. App. Math., 2: 482, the local homology algorithm described in Neddleman and Wunsch, 1970, J. Mol. Biol., 48: 443, the similarity search method described in Pearson and Lipman, 1988, Proc. Natl. Acad. Sci. USA, 85: 2444, and by computer software using these algorithms (GAP, BESTFIT, FASTA and TFASTA in the Wisconsin Genetics Software Package, Genetics Computer Group, 575 Science Dr., Madison, WI), or by BLAST N or BLAST P comparison software.

The term "antibody" as used herein is used in the broadest sense and covers complete monoclonal antibodies, polyclonal antibodies, and multispecific antibodies formed from at least two complete antibodies (e.g., bispecific antibodies), so long as they exhibit the desired biological activity.

The term "monoclonal antibody" as used herein refers to an antibody obtained from a population of substantially homogeneous antibodies, i.e., the individual antibodies constituting the population are identical except for possible naturally occurring mutations that may be present in minor amounts. Monoclonal antibodies are highly specific to a single antigenic determinant (epitope), and in contrast, polyclonal antibodies include different antibodies directed against different determinants (epitopes). Besides specificity, monoclonal antibodies are advantageous in that they can be synthesized without contamination by other antibodies. Here the modifier "monoclonal" indicates the character of the antibody as being obtained from a substantially homogeneous population of antibodies, and is not to be construed as requiring any particular production method.

The monoclonal antibodies in the present invention specifically include chimeric antibodies in which a portion of the heavy and/or light chain is identical or homologous to corresponding sequences in antibodies of a certain species, a certain class, or a certain subclass, while the remainder of the chain(s) is identical or homologous to corresponding sequences in antibodies of another species, another class, or another subclass, so long as they exhibit the desired biological activity (see e.g. U.S. Pat. No. 4,816,567; and Morrison et al., (1984) Proc. Natl. Acad. Sci. USA, 81: 6851-6855). Chimeric antibodies that can be used in the present invention include primatized antibodies comprising variable domain antigen-binding sequences from a non-human primate (e.g., old world monkey, gorilla, etc.) and human constant region sequences.

The term "antibody fragments" refers to a portion of an antibody, preferably the antigen-binding or variable region thereof. Examples of antibody fragments include Fab, Fab', F(ab')$_2$, and Fv fragments; diabodies; linear antibodies; and single-chain Fv.

The terms "bispecific antibody" and "bifunctional antibody conjugate" are used interchangeably, and refer to a conjugate formed by a first antibody (fragment) and a second antibody (fragment) through a coupling arm, and the activity of the respective antibodies is remained in the conjugate, which thus has a dual function and dual specificity.

The term "multispecific antibody" includes, for example, tri- and tetra-specific antibodies, the former is an antibody having three different types of antigen-binding specificity, and the latter is one having four different types of antigen-binding specificity.

The term "intact antibody" refers to an antibody comprising an antigen-binding variable region, as well as a light chain constant domain (CL) and heavy chain constant domains (CH1, CH2 and CH3). The constant domains may be native sequences (e.g., human native sequence constant domains) or amino acid sequence variants thereof. An intact antibody having one or more effector functions is preferred.

"Humanized" forms of non-human (e.g., mouse) antibodies refer to chimeric antibodies that contain minimal sequence derived from non-human immunoglobulin. Most humanized antibodies are human immunoglobulins (donor antibody) in which residues from a hypervariable region are replaced by residues from a hypervariable region of a non-human (e.g., mouse, rat, rabbit or nonhuman primate) species (donor antibody) having the desired specificity, affinity, and capacity. In some embodiments, framework region (FR) residues of the human immunoglobulin are also replaced by non-human residues. Furthermore, humanized antibodies may comprise residues that are not found in the recipient antibody or in the donor antibody. These modifications are made to further refine antibody performance. A humanized antibody generally comprises at least one, and typically two variable domains, in which all or substantially all of the hypervariable loops correspond to those of a non-human immunoglobulin, and all or substantially all of the FRs are those of a human immunoglobulin sequence. The humanized antibody can also comprise at least a portion of an immunoglobulin constant region (Fc, typically Fc of a human immunoglobulin). For details, see e.g., Jones et al., 1986, Nature, 321: 522-525; Riechmann et al., 1988, Nature, 332: 323-329; and Presta, 1992, Curr. Op. Struct. Bwl 2: 593-596.

Depending on the amino acid sequence of the constant domain of their heavy chains, intact antibodies can be assigned to different "classes". The five major classes are IgA, IgD, IgE, IgG, and IgM, and several of these may be further divided into "subclasses" (isotypes), e.g., IgG1, IgG2, IgG3, IgG4, IgA1, and IgA2. The heavy-chain constant domains of different classes of antibodies are known as α, δ, ε, γ, and μ, respectively. The subunit structures and three-dimensional configurations of different classes of immunoglobulins are well known in the art.

In the present invention, although amino acid substitutions in antibodies are substitutions with L-amino acids in most cases, they are not limited thereto. In some embodiments, the peptides may comprise one or more D-amino acids. Peptides containing D-amino acids are thought to be more stable and less prone to degradation in oral cavity, gut or plasma than peptides composed exclusively of L-amino acids.

Monoclonal antibodies used in the present invention can be produced by various methods. For example, monoclonal antibodies for use in the present invention can be obtained by a hybridoma method using various species (including cells of mice, hamsters, rats and human) (see e.g., Kohler et al., 1975, Nature, 256: 495), or by a recombinant DNA technology (see e.g., U.S. Pat. No. 4,816,567), or by isolation from phage antibody libraries (see e.g., Clackson et al., 1991, Nature, 352: 624-628; and Marks et al., 1991, J. Mol. Biol., 222: 581-597).

The preferred antibody used in the present invention is an anti-human ErbB2 antibody, and preferably, the CDR1, CDR2 and/or CDR3 of the anti-human ErbB2 antibody are the CDR1, CDR2 and/or CDR3 of Trastuzumab, respectively. The anti-human ErbB2 antibody can be a humanized antibody or a fully human antibody.

More preferably, the antibody used in the present invention is a humanized mouse anti-human Her2 antibody 4D5 shown in FIG. 1 of U.S. Pat. No. 5,821,337.

Particularly preferably, the antibody used in the present invention is Trastuzumab, the sequence of which has been disclosed in e.g., CN 103319599A. The Lys at the end of the heavy chain of Trastuzumab is apt to delete, which, however, does not affect biological activity, see Dick, L. W. et al., Biotechnol. Bioeng., 100: 1132-1143. Trastuzumab, the sequence thereof wherein the Lys at the end of the heavy chain is deleted, or fragment thereof, as mentioned above, are all within the scope of Trastuzumab of the present invention.

Trastuzumab heavy chain sequence (SEQ ID NO: 1) is:

EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

Trastuzumab light chain sequence (SEQ ID NO: 2) is:

DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Antibody fragments can be produced by various methods, e.g., by proteolytic digestion of intact antibodies (see e.g., Morimoto et al., 1992, Journal of Biochemical and Biophysical Methods, 24: 107-117; and Brennan et al., 1985, Science 229: 81), or directly by recombinant host cells and the antibody phage libraries discussed above. Alternatively, Fab'-SH fragments can be directly recovered from E. coli, and chemically coupled to form F(ab')$_2$ fragments (Carter et al., Biotechnology (NY), February 1992, 10(2): 163-167). In addition, F(ab')$_2$ fragments can be isolated directly from recombinant host cell culture. Other techniques for the production of antibody fragments will be apparent to the skilled practitioner. In some embodiments, the antibody fragment used in the present invention is a single chain Fv fragment (scFv) (see e.g., WO 93/16185; U.S. Pat. Nos. 5,571,894; and 5,587,458). In some embodiments, the antibody fragment is a linear antibody fragment (see e.g., U.S. Pat. No. 5,641,870), which may be monospecific or bispecific.

Bispecific antibodies with binding specificities for at least two different epitopes (see e.g., Millstein et al., 1983, Nature, 305: 537-539) can bind to two different epitopes of the ErbB2 protein. Other bispecific antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to ErbB2-expressing cells. Bispecific antibodies may also be used to localize cytotoxic agents to ErbB2-expressing cells (see e.g., WO 96/16673, U.S. Pat. No. 5,837,234, WO98/02463 and U.S. Pat. No. 5,821,337). Purification methods for bispecific antibodies have been disclosed (see e.g., WO 93/08829; Traunecker et al., 1991, EMBO J. 10: 3655-3659; WO 94/04690; Suresh et al., 1986, Methods in Enzymology, 121: 210; U.S. Pat. No. 5,731,168). Bispecific antibodies can be produced using leucine zippers (see e.g., Kostelny et al., 1992, J. Immunol., 148(5): 1547-1553), and single-chain Fv (sFv) dimers (see e.g., Gruber et al., 1994, J. Immunol. 152: 5368).

Techniques for generating bispecific antibodies from antibody fragments have been described, such as those using chemical linkage wherein intact antibodies are proteolytically cleaved to generate F(ab')$_2$ fragments (Brennan et al., 1985, Science, 229: 81). Fab'-SH fragments can be recovered from E. coli and chemically coupled to form bispecific antibodies (see Shalaby et al., 1992, J. Exp. Med. 175: 217-225). The "diabody" technology provides an alternative method for making bispecific antibody fragments (see Hollinger et al., 1993, Proc. Natl. Acad. Sci. USA, 90: 6444-6448).

Antibodies with more than two valencies can be prepared. Multivalent "octopus" antibodies with three or more antigen binding sites and two or more variable domains can be readily produced by recombinant expression of nucleic acid encoding the polypeptide chains of the antibodies (see e.g., US 2002/0004586 and WO 01/77342). For example, trispecific antibodies can be prepared (see e.g., Tutt et al., 1991, J. Immunol., 147: 60). The CH3 domains of a trispecific or tetraspecific antibody (in the heavy chain or in the modified heavy chain) can be altered by the "knob-into-holes" technology which is described in detail with several examples in e.g., WO 96/027011, Ridgway, J. B. et al., 1996, Protein Eng., 9: 617-621; and Merchant, A. M. et al., 1998, Nat. Biotechnol., 16: 677-681. In this method, the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge further stabilizes the heterodimers (see e.g., Merchant, A. M. et al., 1998, Nature Biotech. 16: 677-681; and Atwell, S. et al., 1997, J. Mol. Biol., 270: 26-35) and increases the yield.

An amino acid sequence is usually altered by altering the underlying nucleic acid sequence. Nucleic acid molecules encoding amino acid sequence variants of an antibody can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. The sites of greatest interest for substitutional mutagenesis include the hypervariable regions, but FR alterations are also contemplated. As in Example 2 of CN103319599A, using conventional molecular biology techniques, site-directed mutagenesis was conducted to total gene synthesized DNA fragments encoding the heavy chain of Trastuzumab, and the heavy chain of Trastuzumab mutant, K30R, was cloned to an heavy chain expression vector, where the operation of digestion and ligation was carried out according to the instructions of commercially available kits.

Drug

The drug used in the present invention is a cytotoxic agent. The term "cytotoxic agent" as used herein refers to a substance that inhibits or prevents the function of cells and/or causes destruction of cells.

In some embodiments, the cytotoxic agent is an auristatin, such as auristatin E (also known as a derivative of dolastatin-10) or a derivative thereof (e.g., an ester formed from auristatin E and a keto acid). For example, auristatin E can be reacted with para-acetyl benzoic acid or benzoylvaleric acid to produce AEB (auristatin EB) and AEVB (5-benzoylvaleric acid auristatin E ester), respectively. Other typical auristatins include AFP (auristatin F phenylene diamine), MMAF (monomethyl auristatin F), and MMAE (monomethyl auristatin E).

The synthesis and structure of exemplary auristatins are described in U.S. Pat. Nos. 6,884,869, 7,098,308, 7,256,257, 7,423,116, 7,498,298 and 7,745,394. The synthesis and structure of other new auristatins are described in WO 2013/173393. These references are incorporated herein by reference in their entirety.

In some embodiments, the cytotoxic agent is an agent of maytansinoids. Maytansine was first isolated by Kupchan et al. from the east African shrub *Maytenus serrata* and shown to be 100- to 1000-fold more cytotoxic than conventional chemotherapeutic agents such as methotrexate, daunorubicin, and vincristine (see U.S. Pat. No. 3,896,111). Subsequently, it was found that some microorganisms also produce maytansinoids such as maytansinol and C-3 esters of maytansinol (see U.S. Pat. No. 4,151,042). Synthetic maytansinol C-3 esters and maytansinol analogues have also been reported (see Kupchan et al., 1978, J. Med. Chem., 21: 31-37; Higashide et al., 1977, Nature, 270: 721-722; Kawai et al., 1984, Chem. Pharm. Bull., 32: 3441-3451). C-3 esters of maytansinol are prepared from maytansinol. Examples of maytansinol analogues include maytansinol modified on the aromatic ring (e.g., dechlorinated) or at the C-15, C-18, C-20 and/or C-4, C-5.

In some embodiments, the cytotoxic agents are, for example, but not limited to, the following compounds:

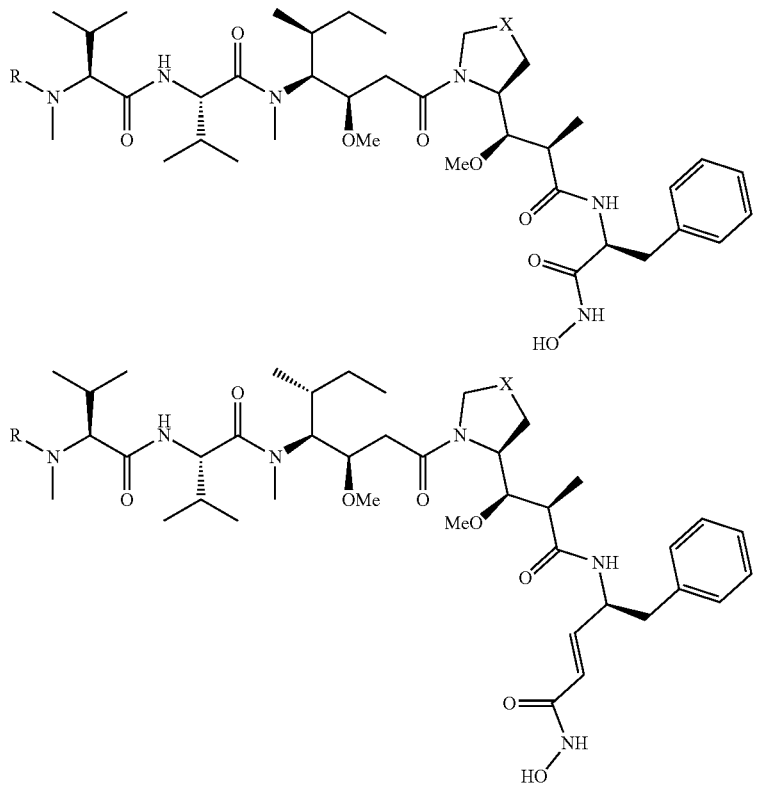

-continued
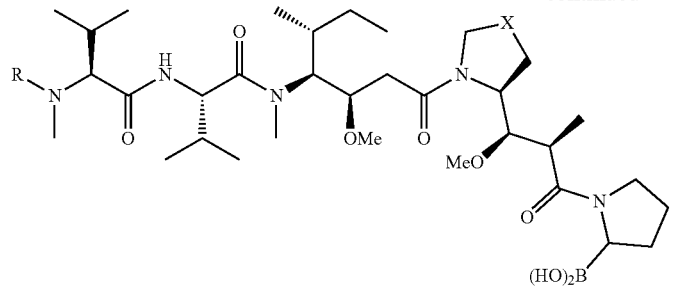
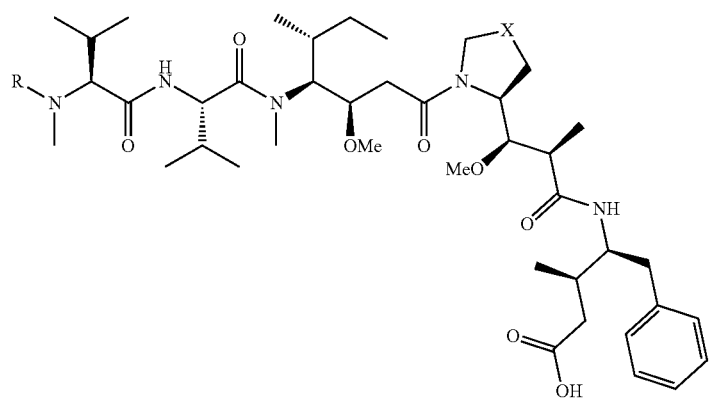
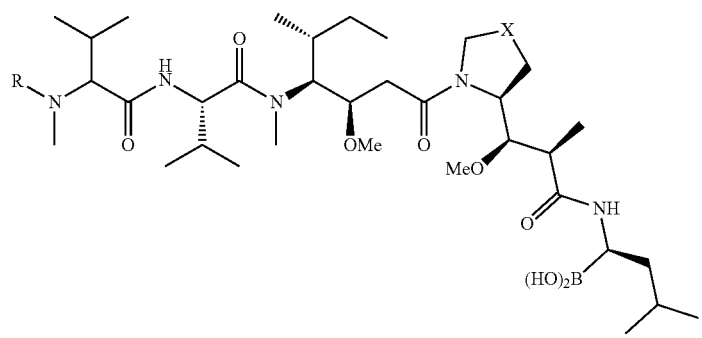
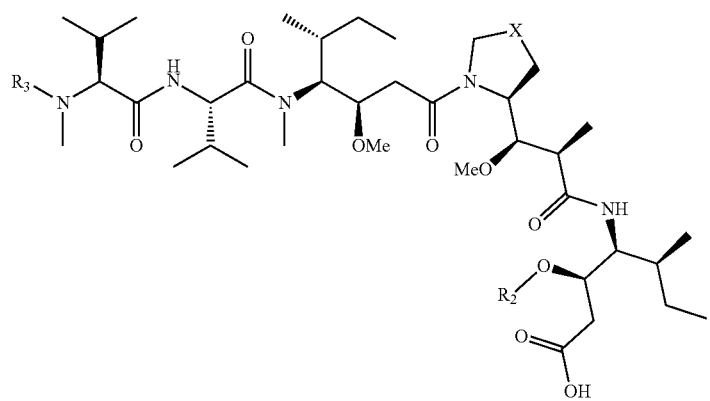

-continued
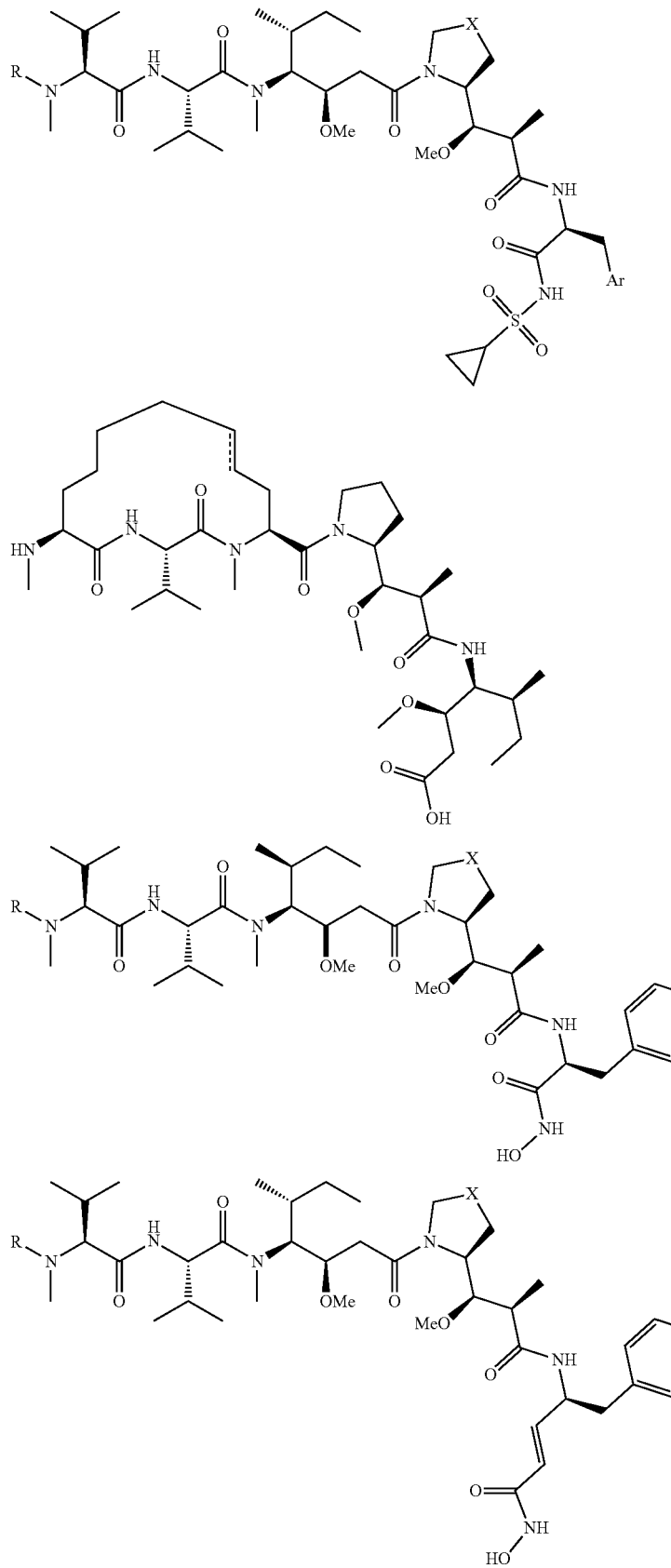

-continued
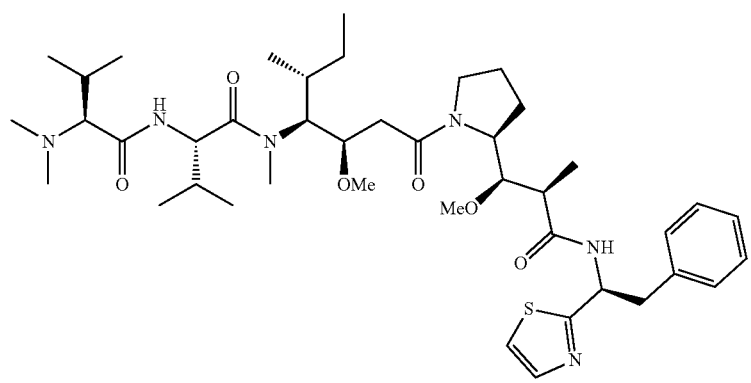
Dolostatin 10
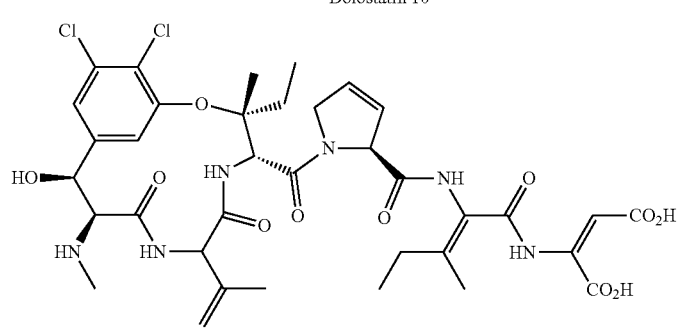
Phomopsin A
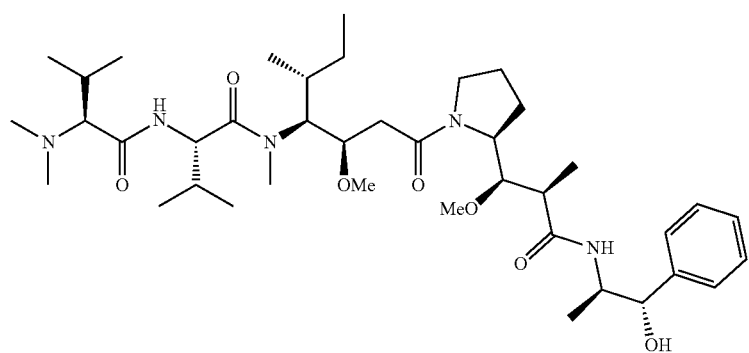
Auristatin E
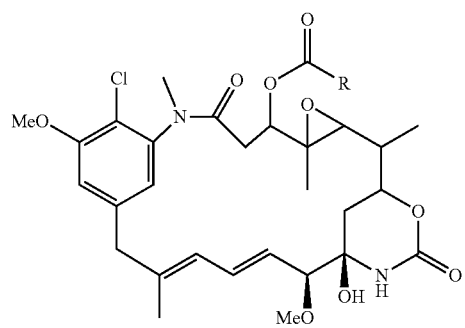
Maytansine -continued
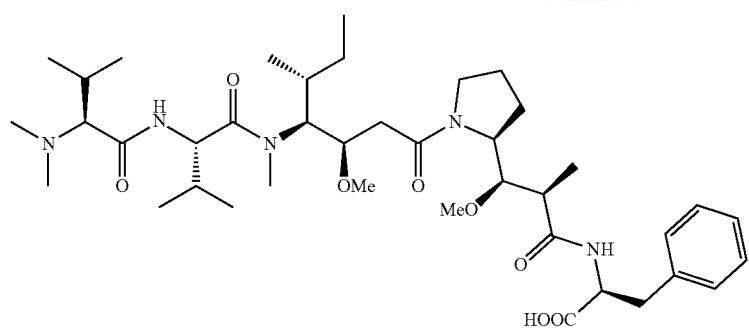
Auristatin F
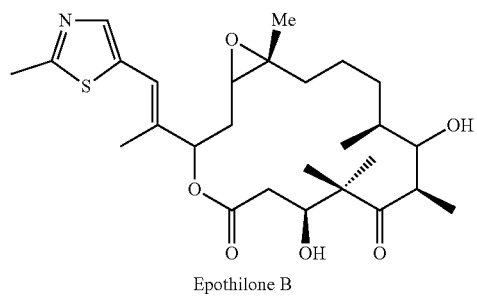
Epothilone B
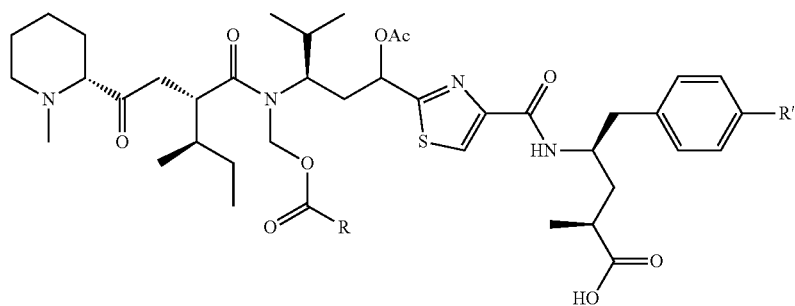
Tubulysins
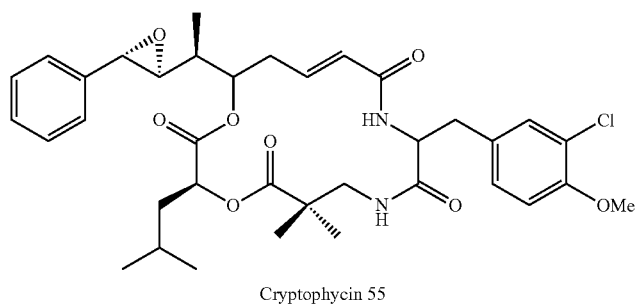
Cryptophycin 55
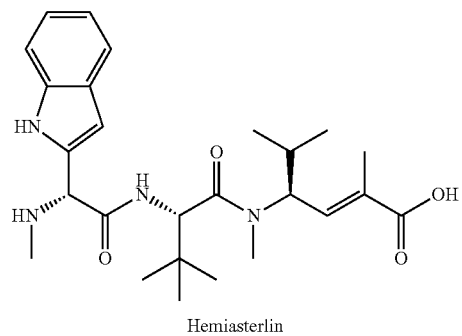
Hemiasterlin

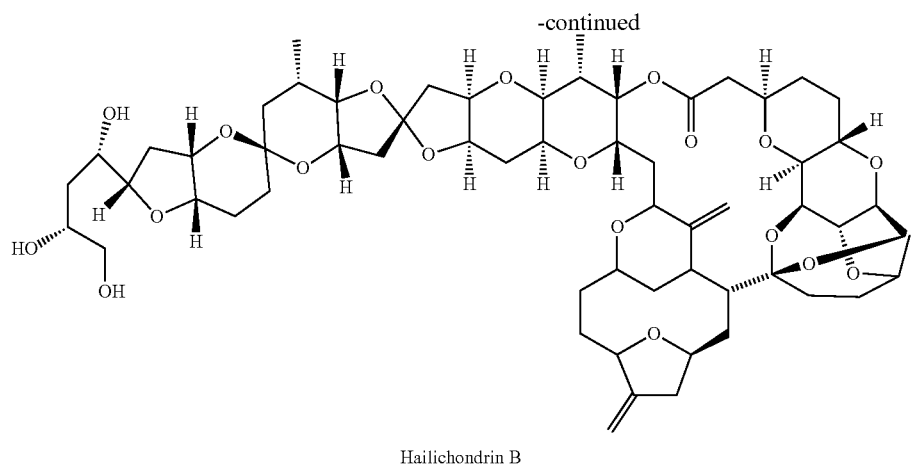

Hailichondrin B

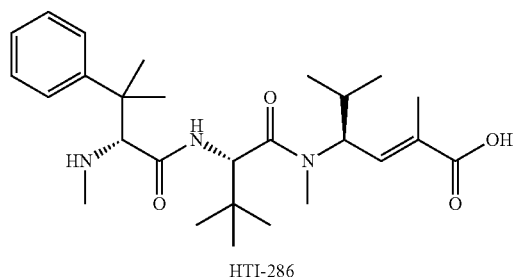

HTI-286 wherein R, $R_1$ and $R_2$ are each independently selected from the group consisting of H, $C_1$-$C_8$ alkyl or $C_3$-$C_8$ cycloalkyl at each occurrence, and the alkyl and cycloalkyl are optionally substituted with one or more (e.g., 1, 2, 3, 4 or 5) substituents selected from halogens (e.g., F, Cl, Br or I); X is —S—, —CH$_2$—, —CH(OH)—, —CH(OR)—, —CH(ONH$_2$)—, or —C(O)—; R' is selected from the group consisting of H, —NH$_2$, Cl, Br, I, —OS(O)$_2$R; and Ar is $C_6$-$C_{14}$ aryl (e.g., phenyl or naphthyl).

In preferred embodiments, the cytotoxic agent group is derived from a compound of Formula (D1) or (D2), or a stereoisomer thereof

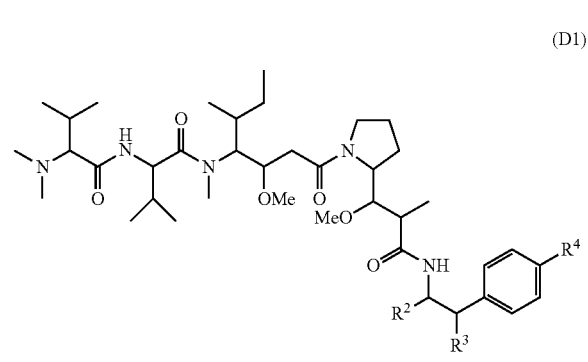

(D1)

wherein:
R$^2$ is selected from the group consisting of —CH$_2$N$_3$, —CONHSO$_2$(cyclopropyl), thiazol-2-yl, —CH$_3$ and —COOH;
R$^3$ is selected from the group consisting of H and —OH; and R$^4$ is selected from the group consisting of H, —NH$_2$, Cl, Br, I, —OS(O)$_2$R$^6$, wherein R$^6$ is H, $C_1$-$C_8$ alkyl, $C_3$-$C_8$ cycloalkyl or $C_6$-$C_{14}$ aryl, and the alkyl, cycloalkyl and aryl are each optionally substituted with one or more (e.g., 1, 2, 3, 4 or 5) substituents selected from halogens such as F;

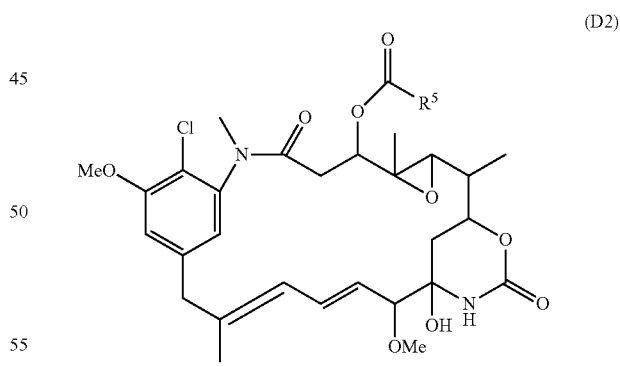

(D2)

wherein R$^5$ is selected from the group consisting of —CH(CH$_3$)N(CH$_3$)C(O)CH$_2$CH$_2$SH and —CH(CH$_3$)N(CH$_3$)C(O)CH$_2$C(CH$_3$)$_2$SH.

In Formula (I), the cytotoxic agent group may be a group obtained by removing R$^4$ or R$^5$, or by removing the hydrogen or R$^6$ in R$^4$ or R$^5$ from the compound of Formula (D1) or (D2).

In preferred embodiments, the cytotoxic agent is selected from:

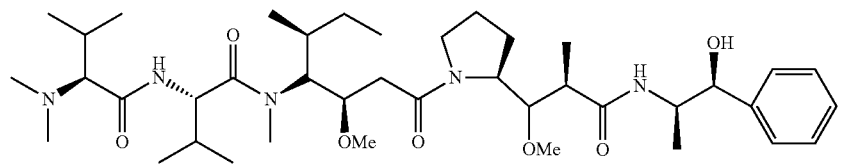
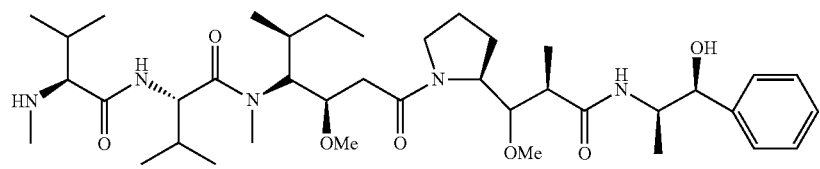
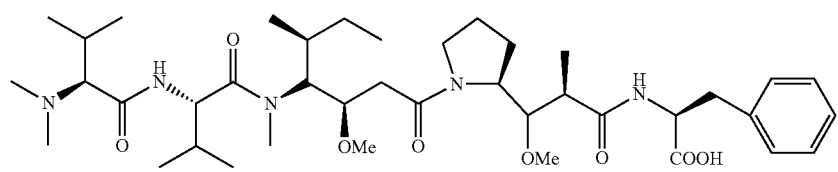
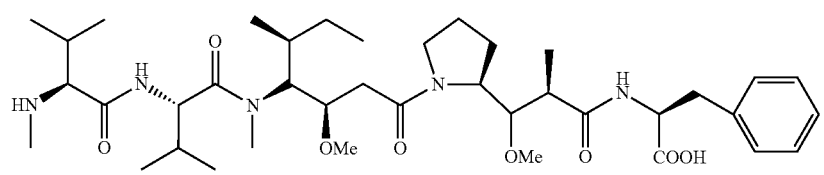
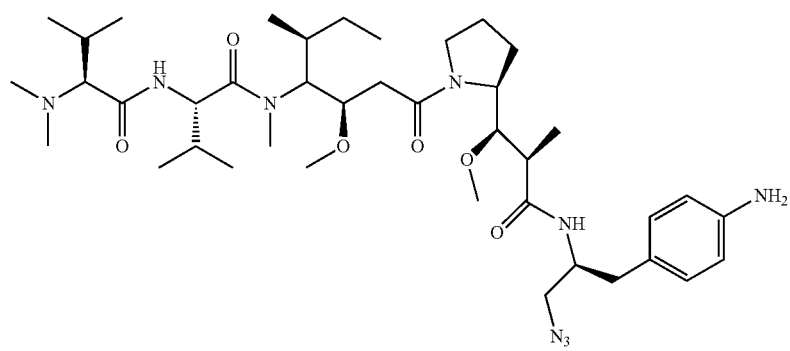
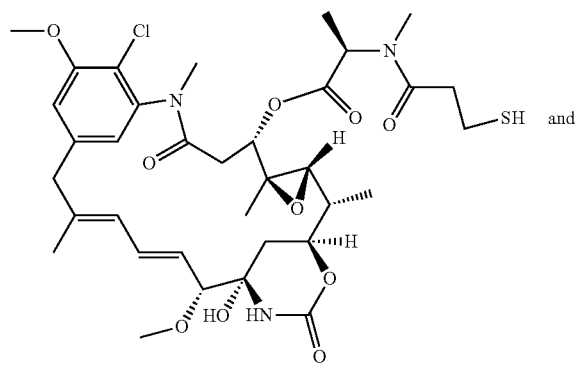
and

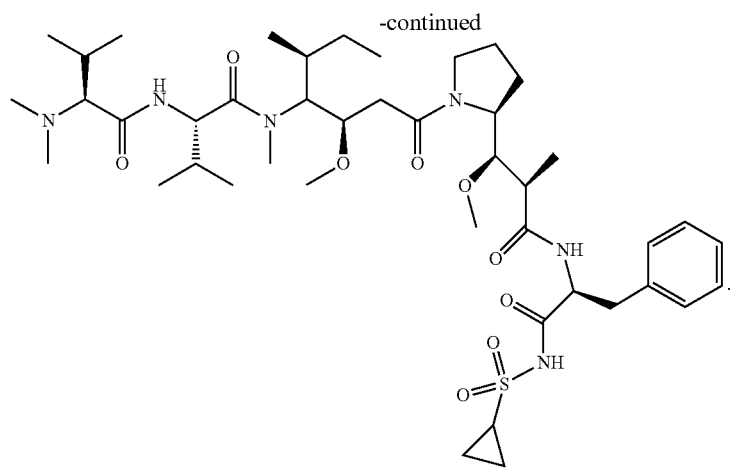

-continued

Linker

In the antibody drug conjugation of the present invention, the cytotoxic agent group is connected to the antibody molecule via a divalent linker.

The conjugation of the linker to the antibody can be accomplished by a variety of ways, e.g., via a lysine residue on the surface of the antibody, or via reductive coupling with an oxidized alkyl group of the antibody. The conjugation can be one based on a hydrazone, disulfide bond or peptide structure. These conjugation ways are known to those skilled in the art.

Linkers useful in the present invention include cleavable and non-cleavable linkers. A cleavable linker is typically susceptible to cleavage under intracellular conditions. Suitable cleavable linkers include, for example, a peptide linker cleavable by an intracellular protease (such as lysosomal protease) or an endosomal protease. In exemplary embodiments, the cleavable linker can be a dipeptide linker, such as a valine-citrulline (val-cit) linker, a phenylalanine-lysine (phe-lys) linker, or a maleimidocaproyl-valine-citrulline-p-aminobenzyloxycarbonyl (mc-Val-Cit-PABA) linker. Other suitable cleavable linkers include linkers hydrolyzable at a specific pH or pH range (such as a hydrazone linker) and a disulfide linker. A non-cleavable linker can be sulfo-SMCC. Sulfo-SMCC is coupled to protein via a maleimide group, and its sulfo-NHS ester can be reacted with a primary amine (such as a Lysine ε-amino and an N-terminal α-amino of a protein or peptide). Yet another non-cleavable linker is maleimidocaproyl (MC). The linker may be covalently bound to the antibody to such an extent that the antibody must be degraded intracellularly in order for the drug to be released.

A linker includes the group for linkage to the antibody, for example, an amino, hydroxyl or carboxyl group. A linker can be derived from, e.g., malemide, haloacetamides (e.g., iodoacetamides, bromoacetamides or chloroacetamides), haloesters (e.g., iodoesters, bromoesters or chloroesters), halomethyl ketones (e.g., iodomethyl ketones, bromomethyl ketones or chloromethyl ketones), benzylic halides (e.g., benzylic iodide, benzylic bromide or benzylic chloride), vinyl sulfone and pyridylthio) (see e.g., Wong, 1991, Chemistry of Protein Conjugation and Cross-linking, CRC Press, Inc., Boca Raton).

In some embodiments, the linkers include at least Val-Cit, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, Ala-PAB or PAB. In some embodiments, the linkers include at least peptides, oligosaccharides, —(CH$_2$)$_n$—, —(CH$_2$CH$_2$O)$_n$—. In some embodiments, the linkers include at least —C(O)—, —NH—C(O)—, —C(O)—O—, —NH—C(O)—NH— or —NH—C(O)—O—.

In some embodiments, the linker L in Formula (I) may be selected from the group consisting of:

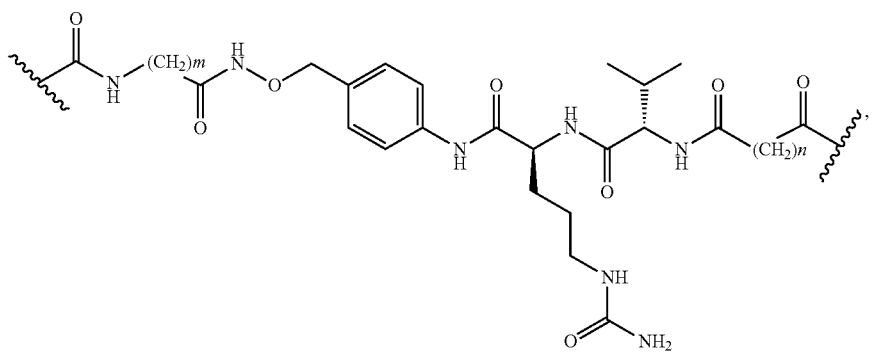

-continued
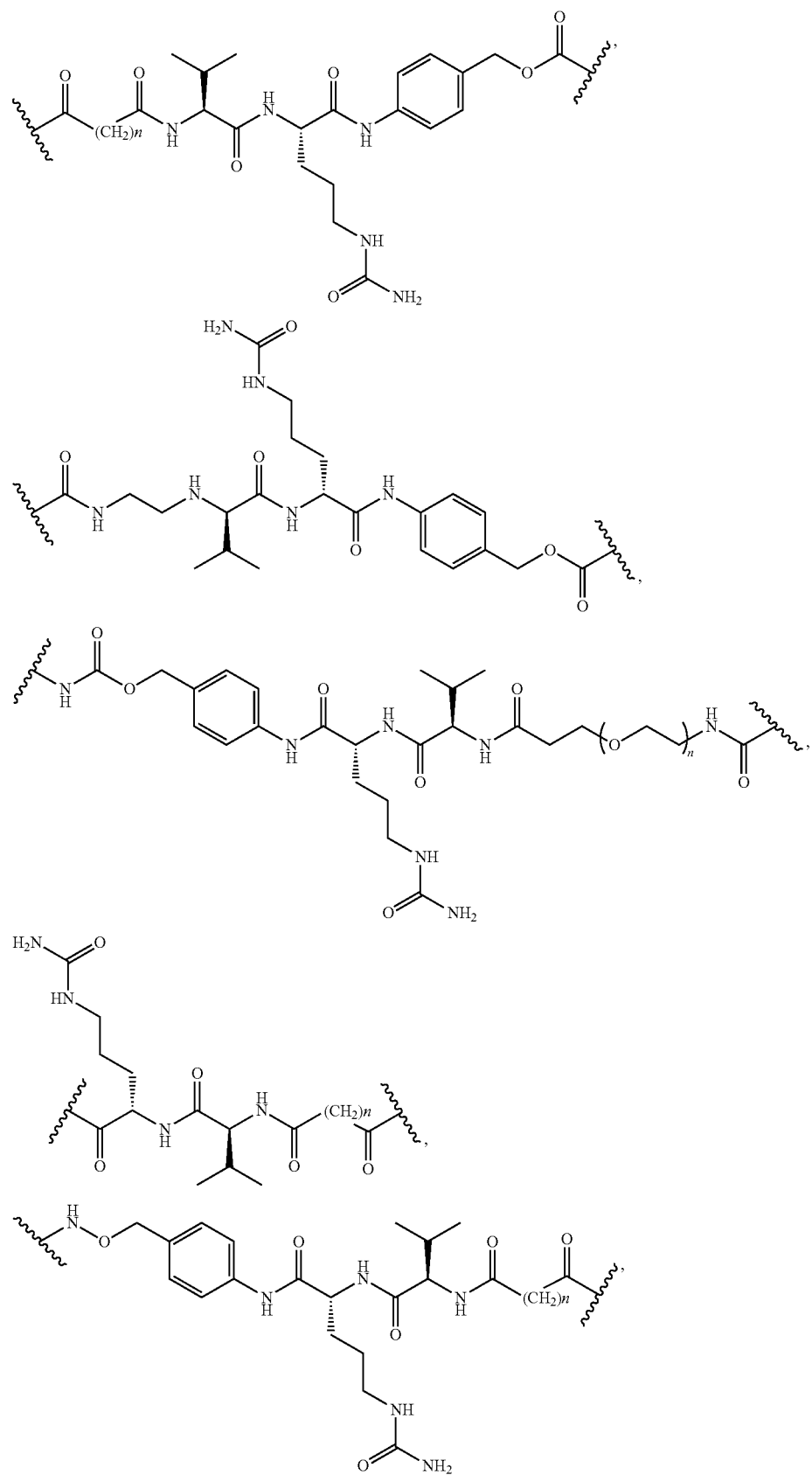

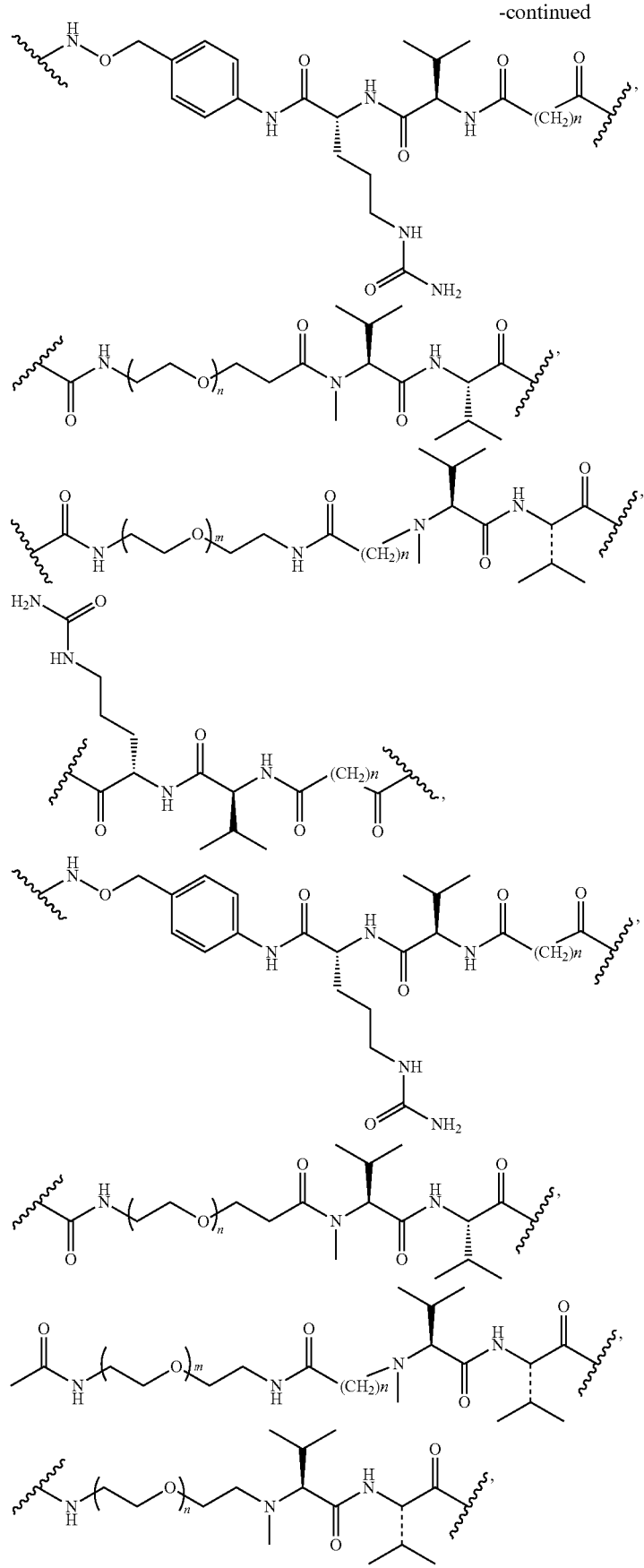

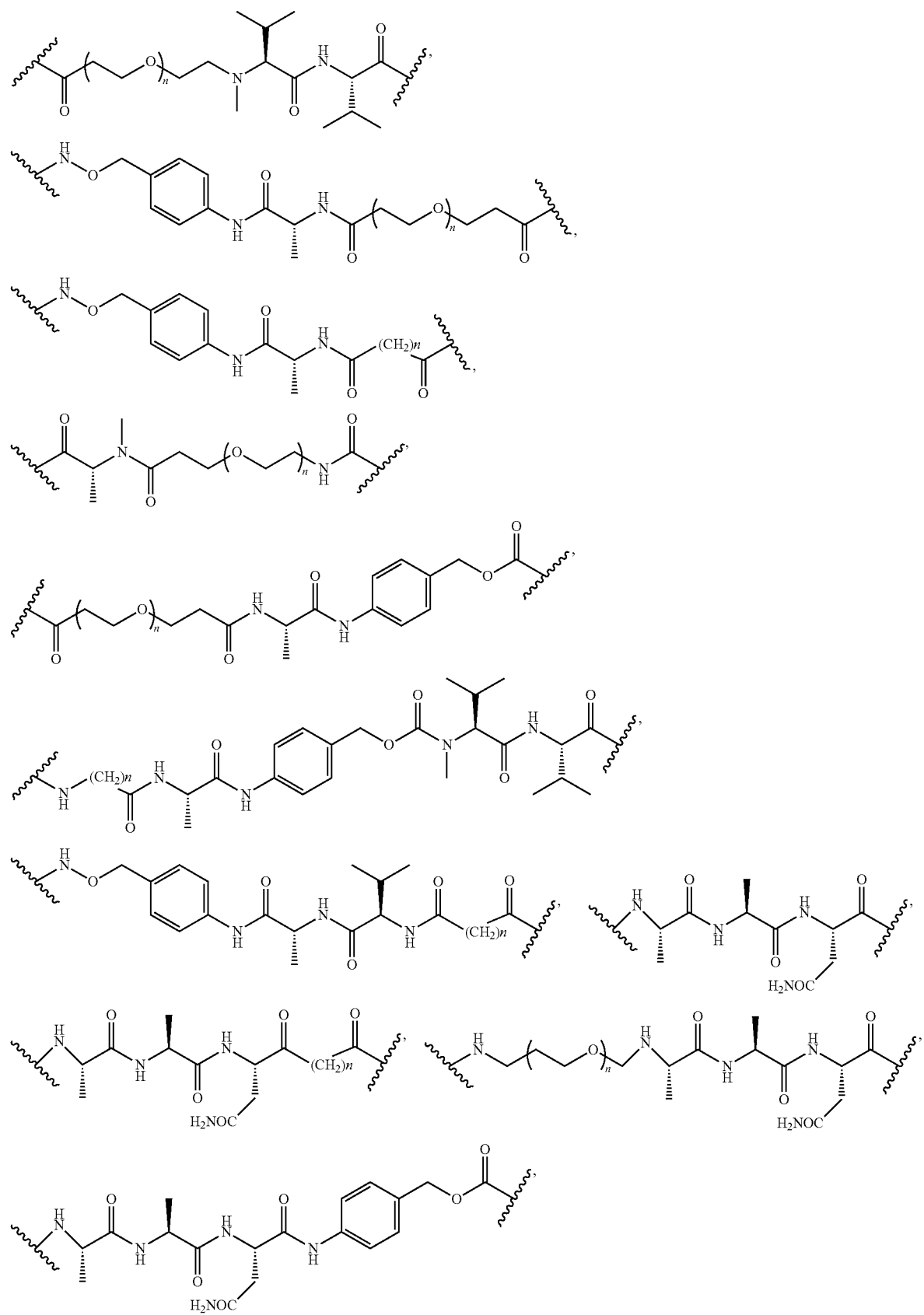

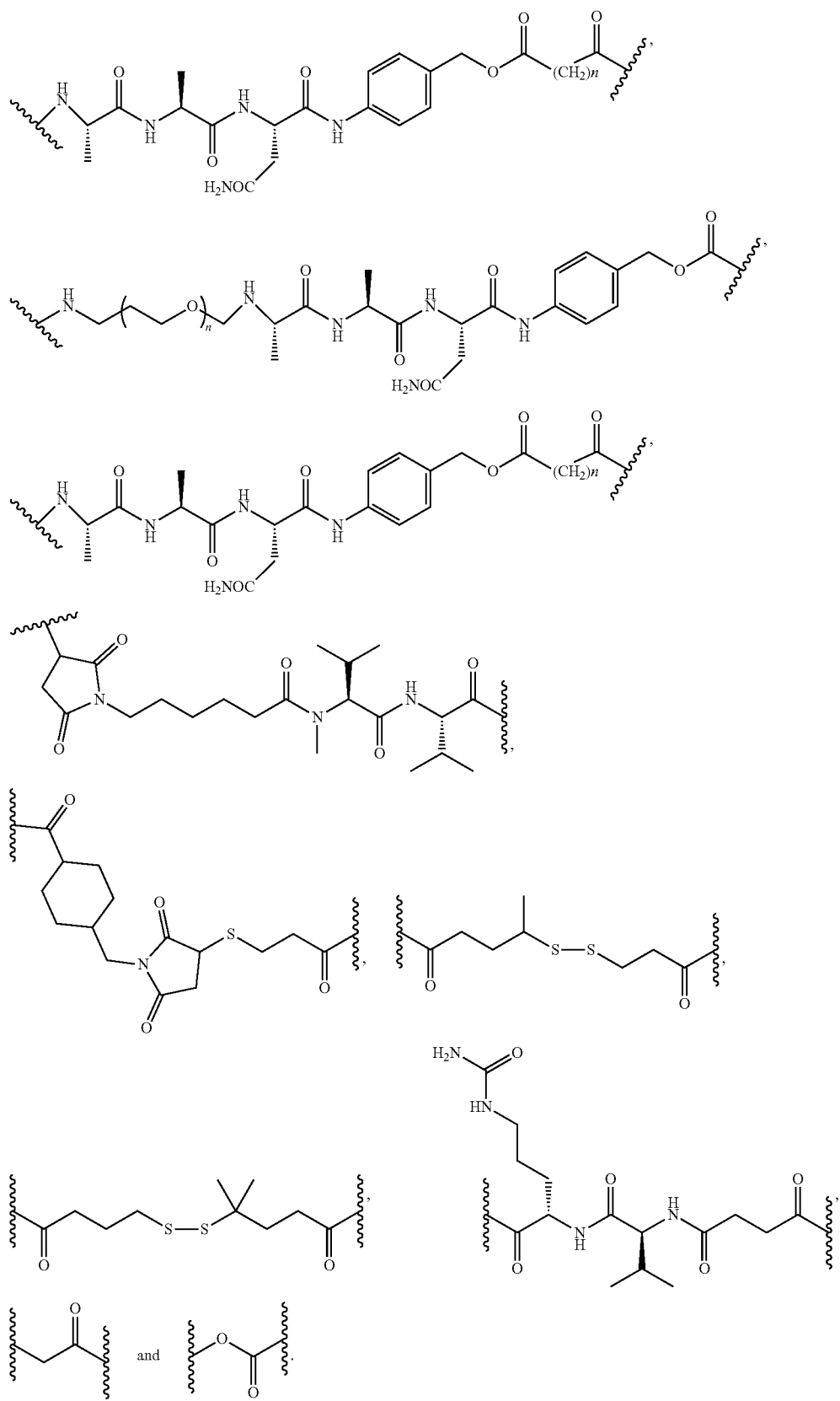

wherein each of m and n is an integer selected from the group consisting of 1-10, preferably 1, 2, 3, 4, 5 or 6 at each occurrence.

Antibody-Drug Conjugate

The antibody-drug conjugate of the first aspect of the present invention is represented by Formula (I) as defined herein above.

The most preferred antibody-drug conjugates of Formula (I) are selected from I-1, I-2 and I-3:

stereoisomers, or metabolites, or solvates, and the salts, stereoisomers, or metabolites can also be in the form of solvates.

The term "pharmaceutically acceptable salts" refers to salts that keep the biological availability and nature of a compound, and meet the requirements for medicines in terms of biological or other aspects. In many cases, the

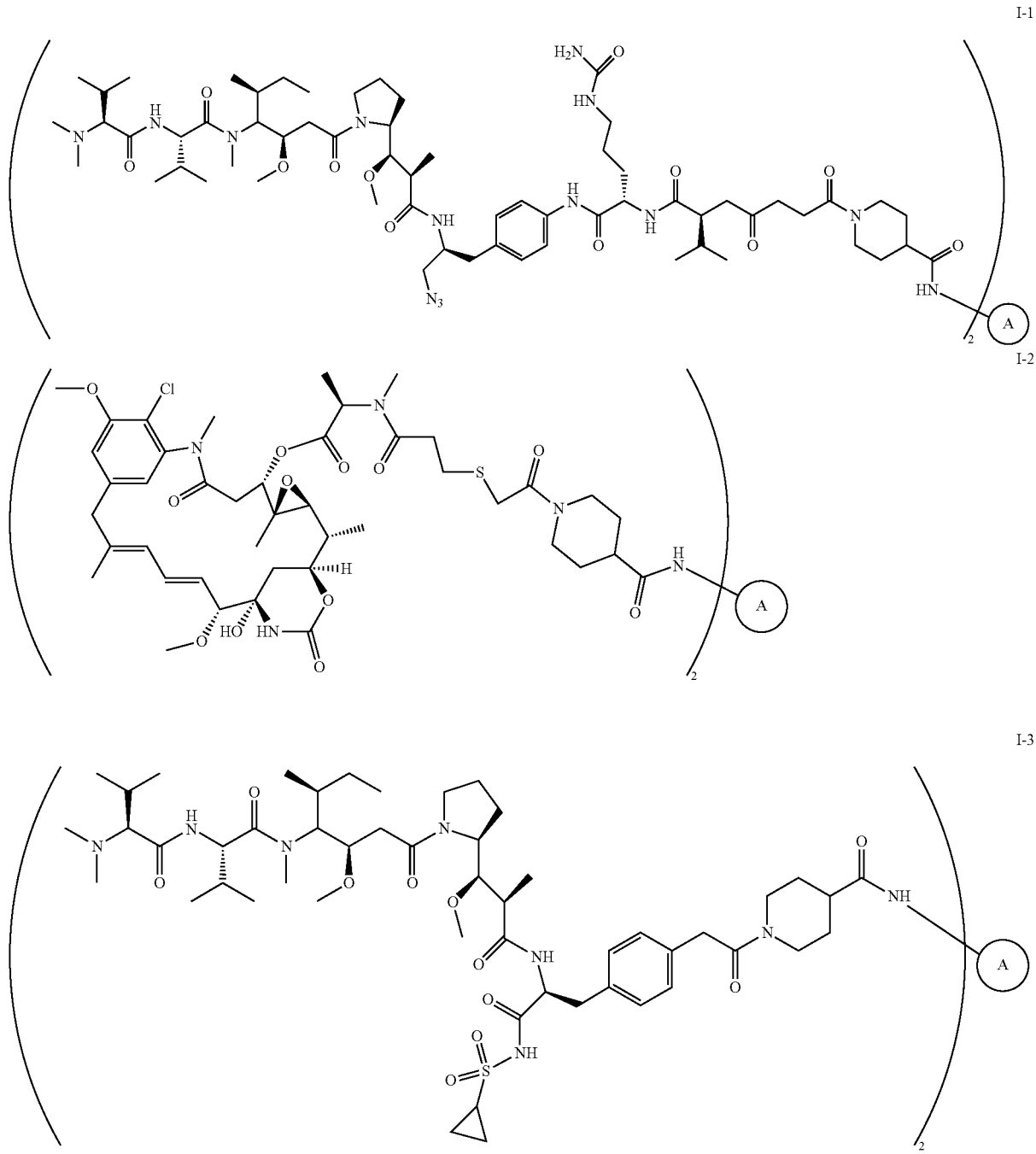

wherein "A" is Trastuzumab.

The antibody-drug conjugates of the present invention can be in the form of pharmaceutically acceptable salts, or antibody-drug conjugates of the present invention form acid addition salts and/or base addition salts via the amino groups and/or carboxyl groups or other similar groups therein.

Pharmaceutically acceptable acid addition salts can be those formed with inorganic acids or organic acids. The inorganic acids include, e.g., hydrochloric acid, hydrobromic acid, sulfuric acid, nitric acid, and phosphorus acid, etc. The organic acids include, e.g., acetic acid, propionic acid, hydroxyacetic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid, etc.

Pharmaceutically acceptable base addition salts can be those formed with inorganic bases or organic bases. The salts formed with inorganic bases include, e.g., sodium salts, potassium salts, lithium salts, ammonium salts, calcium salts, magnesium salts, iron salts, zinc salts, copper salt, manganese salts, and aluminium salts, etc., and ammonium salts, potassium salts, sodium salts, calcium salts, and magnesium salts are particularly preferred. The organic bases include, e.g., primary amines, secondary amines, and tertiary amines, substituted amines (including naturally occurring substituted amines), cyclamines, basic ion exchange resins, etc. Specific examples of organic bases are isopropylamine, trimethylamine, diethylamine, N-ethylethanamine, tripropylamine and ethanolamine The term "stereoisomers" refers to isomers formed due to the existence of at least one asymmetric center. A compound with one or more asymmetric centers can form a racemate, a racemic mixture, a single enantiomer, a diastereomeric mixture and a single diastereomer. Specific individual molecules may be present as geometric isomers (cis-/trans-). Unless otherwise specified, when a name or structure of a compound having one or more asymmetric centers is disclosed without specifically indicating the stereochemistry, it should be understood that all the possible stereoisomers of the compounds are contemplated.

The term "solvates" refers to the solvates formed by one or more solvent molecules and any of the antibody-drug conjugates of Formula I or pharmaceutically acceptable salts or isomers thereof. The term "solvates" includes hydrates (e.g., hemihydrate, monohydrate, dihydrate, trihydrate, tetrahydrate and similar hydrates).

The term "metabolites" refers to the substances generated via oxidation, reduction, hydrolysis, amidation, deamidation, esterification and/or enzymolysis in vivo upon administration.

The antibody-drug conjugates of the present invention can selectively deliver an effective amount of cytotoxic agents to tumor tissue, thereby offering better therapeutic selectivity, and achieving desired efficacy with a lower dose.

In the second aspect, the present invention provides a preparation method of the antibody-drug conjugate of the first aspect, comprising the steps of:

(1) preparing a compound of Formula (I-A):

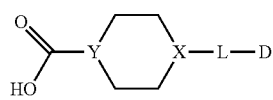

(I-A)

wherein D, L, X and Y are as defined in Formula (I) above;

(2) obtaining a compound of Formula (I-A-G) by activating the compound of Formula (I-A) from step (1)

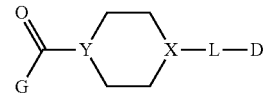

(I-A-G)

wherein G is selected from the group consisting of —F, —Cl, —Br, —I, —N$_3$, —OR, —SR, —ONRR', RC(O)O—, —OP(O)RR', RSO$_2$—O— and

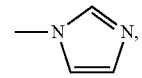

wherein each of R and R' at each occurrence is independently C$_1$-C$_{10}$ alkyl, C$_6$-C$_{14}$ aryl, heterocyclyl having 5 to 10 ring members, or phenoxy, and each of the alkyl, aryl, heterocyclyl and phenoxy is unsubstituted or independently substituted with one or more substituents selected from the group consisting of halogen, hydroxyl, C$_1$-C$_4$ alkyl, C$_1$-C$_4$ alkoxy, C$_3$-C$_8$ cycloalkyl, heterocyclyl having 5 to 8 ring members, C$_6$-C$_{10}$ aryl or heteroaryl having 5 to 10 ring members;

(3) obtaining a mixture of a variety of antibody-drug conjugates having different a values by conjugating the compound of Formula (I-A-G) from step (2) with the anti-ErbB2 antibody or active fragment or variant thereof; and (4) obtaining the antibody-drug conjugate by purifying the mixture from step (3) with one or more chromatographic methods selected from the group consisting of ion exchange chromatography, hydrophobic chromatography, reverse phase chromatography and affinity chromatography.

Preferably, the group G in Formula (I-A-G) in step (2) is selected from the group consisting of —ONRR' and —OP(O)RR', wherein each of R and R' at each occurrence is independently phenoxy.

More preferably, the compound of Formula (I-A-G) in step (2) is a compound of Formula (I-B) formed by reacting pentafluorophenol with the compound of Formula (I-A):

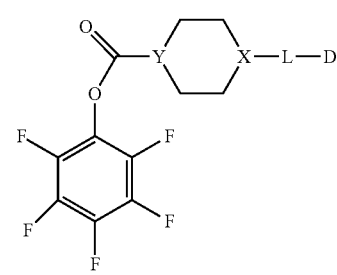

(I-B)

wherein D, L, X and Y are as defined in Formula (I) above, and the reaction is performed preferably using EDCI, NHS and/or DCM.

Preferably, the purification in step (4) is performed by HPLC.

In the third aspect, the present invention provides a pharmaceutical composition comprising the antibody-drug conjugate of the first aspect of the present invention or a pharmaceutically acceptable salt, stereoisomer or metabolite thereof, or a solvate of the foregoing, and a pharmaceutically acceptable carrier. Optionally, the pharmaceutical compositions further comprising one or more other anticancer agents, such as chemotherapeutic agents and/or antibodies.

The term "pharmaceutical composition" used herein refers to a combination of at least one active ingredient and a pharmaceutically acceptable carrier and/or excipient for a specific purpose. In some embodiments, the pharmaceutical composition is in the form of a mixture of various ingredients, while in some other embodiments, the various ingredients of the pharmaceutical composition can be separate in terms of time and/or space, provided that they can work together to achieve the object of the present invention.

When two or more active ingredients are comprised in the pharmaceutical composition, the active ingredients can be applied simultaneously as a mixture to a subject, or can be applied separately to the subject. When applied separately, the active ingredients can be applied simultaneously or sequentially.

The selection of the pharmaceutically acceptable carrier depends on the dosage form of the pharmaceutical composition, first the administration route of the dosage form (e.g. for oral, nasal, intradermal, subcutaneous, intramuscular or intravenous infusion), and second the formula of the dosage form. For example, the pharmaceutically acceptable carrier can include water (e.g., water for injection), buffer solution, isotonic salt solution such as PBS (phosphate buffered saline), glucose, mannitol, dextrose, lactose, amylum, magnesium stearate, cellulose, magnesium carbonate, 0.3% glycerin, hyaluronic acid, ascorbic acid, lactic acid, alcohol, polyalkylene glycol such as polyethylene glycol (e.g., polyethylene glycol 4000) or polypropylene glycol, triglyceride etc.

In addition, the pharmaceutical composition of the present invention can comprised various additives such as wetting agents, emulsifiers or buffers as needed.

In the fourth aspect, the present invention provides use of the antibody-drug conjugate of the first aspect of the present invention or a pharmaceutically acceptable salt, stereoisomer or metabolite thereof, or a solvate of the foregoing in the manufacture of a medicament for the prophylaxis or treatment of cancer. The cancer is as described hereinafter in the sixth aspect of the present invention, e.g., including but not limited to breast cancer, gastric cancer, ovarian cancer, non-small cell lung cancer and liver cancer, especially breast cancer, e.g., breast cancer with high expression of ErbB2.

In the fifth aspect, the present invention provides a pharmaceutical preparation comprising the antibody-drug conjugate of the first aspect of the present invention or a pharmaceutically acceptable salt, stereoisomer or metabolite thereof, or a solvate of the foregoing.

Preferably, the pharmaceutical preparation is in the form of a solid preparation, a semi-solid preparation, a liquid preparation or a gas preparation. The pharmaceutical is especially preferably lyophilized powder for injection, which has the advantages of less auxiliary materials, good stability and high safety in clinical use.

In the sixth aspect, the present invention provides a method for the prophylaxis or treatment of cancer, comprising administering to a patient in need thereof the antibody-drug conjugate of the first aspect of the present invention, a pharmaceutically acceptable salt, stereoisomer or metabolite thereof, or a solvate of the foregoing, or administering to a patient in need thereof the pharmaceutical composition of the third aspect of the present invention or the pharmaceutical preparation of the fifth aspect of the present invention. Optionally, the method further comprises administering to patient one or more other anticancer agents, such as chemotherapeutic agents and/or antibodies, which can be administered simultaneously or sequentially with the antibody-drug conjugate, pharmaceutical composition or pharmaceutical preparation of the present invention.

The cancer includes but is not limited to carcinoma, blastoma, sarcoma, leukemia, lymphoma and other malignant lymphatic diseases. Specific examples of the cancer include: squamous cell carcinoma (e.g., squamous epithelial cell carcinoma), lung cancer (e.g., small cell lung cancer, non-small cell lung cancer (NSCLC), lung adenocarcinoma and lung squamous cell carcinoma), peritoneal cancer, and gastric or stomach cancer (e.g., gastrointestinal cancer and gastrointestinal stromal tumor (GIST)), pancreatic cancer, malignant glioma, cervical cancer, ovarian cancer, bladder cancer, breast cancer, colon cancer, rectal cancer, colorectal cancer, endometrial cancer or uterine cancer, salivary gland cancer, renal cancer, prostate cancer, vaginal cancer, thyroid cancer, liver cancer, anal cancer, penile cancer, and head and neck cancer. Particularly, the cancer is one with high expression of ErbB2, such as breast cancer, gastric cancer, endometrial cancer, salivary gland cancer, lung cancer, kidney cancer, colon cancer, thyroid cancer, pancreatic cancer or bladder cancer.

The present invention will be further illustrated by the following examples. These examples are used to illustrate the present invention only, but not limit the present invention in any way.

EXAMPLES

The meanings of the abbreviations used in each example are shown in the following table:

| | |
|---|---|
| DMF | dimethylformamide |
| DIC | diisopropyl carbodiimide |
| HOAt | 1-hydroxyl-7-azabenzotriazole |
| EtOAc | ethyl acetate |
| DIEA | diisopropylethylamine |
| HATU | 2-(1H-7-azabenzotriazol-1-yl)-1,1,3,3-tetramethyluronium hexafluorophosphate |
| PyBOP | 1H-Benzotriazol-1-yl-oxy-tripyrrolidinophosphonium hexafluorophosphate |
| HOBT | 1-hydroxyl-benzotriazole |
| LiOH | lithium hydrate |
| DCM | dichloromethane |
| EDCI | 1-ethyl-3-(3-dimethyl-amino-propyl)-carbodiimide |
| NHS | N-hydroxyl succinimide |
| DMA | N,N-dimethylacetamide |
| HIC | Hydrophobic interaction chromatography |
| HPLC | High performance liquid chromatography |
| UPLC | Ultra-high performance liquid chromatography |
| THF | Tetrahydrofuran |
| EtOAc | ethyl acetate |

Example 1. Preparation of Antibody-Drug Conjugate I-1

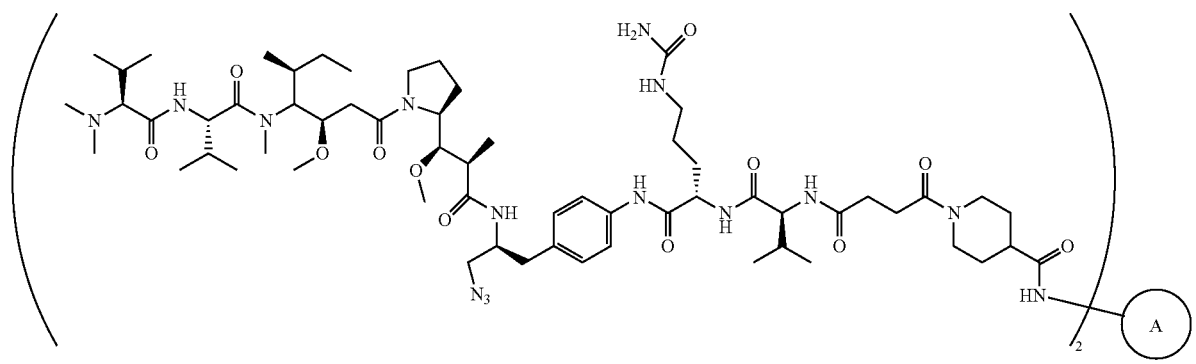

I-1

Step a. Preparation of Intermediate D-I

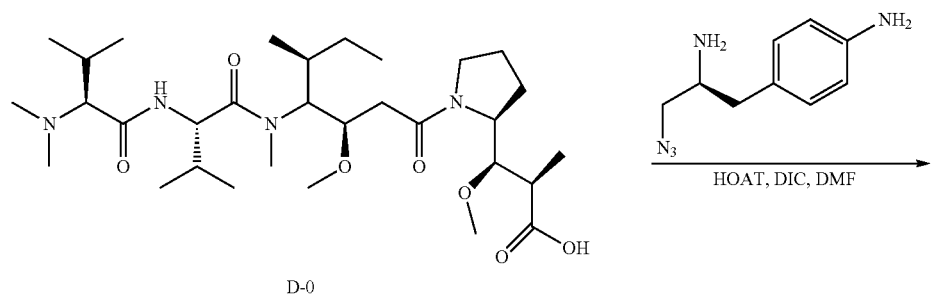

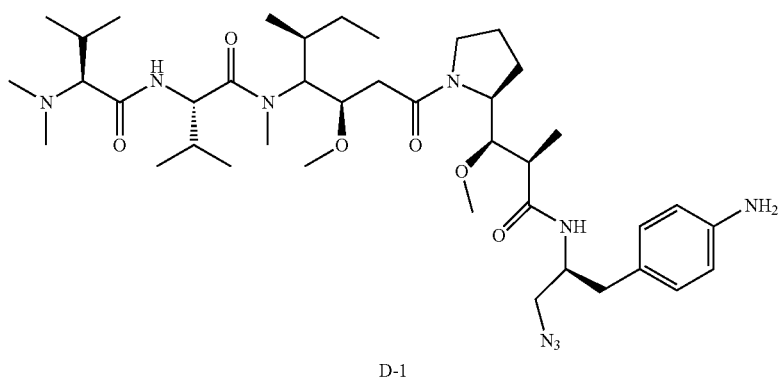

At room temperature, Compound D-0 (1 mmol, 1 eq.) was dissolved in DMF (50 ml), and DIC (1.1 eq.), HOAt (1.1 eq.) and 4-(3-azido-2-aminopropyl)aniline (1.5 eq.) were added successively. The reaction mixture was stirred for 8 hours at room temperature, and then water (600 ml) and EtOAc (200 ml*3) were added. After extraction, the organic phase was collected, concentrated and purified by HPLC to obtain Intermediate D-1.

MS m/z (ESI): 773 [M+H]$^+$.

Step b. Preparation of Intermediate I-A-1

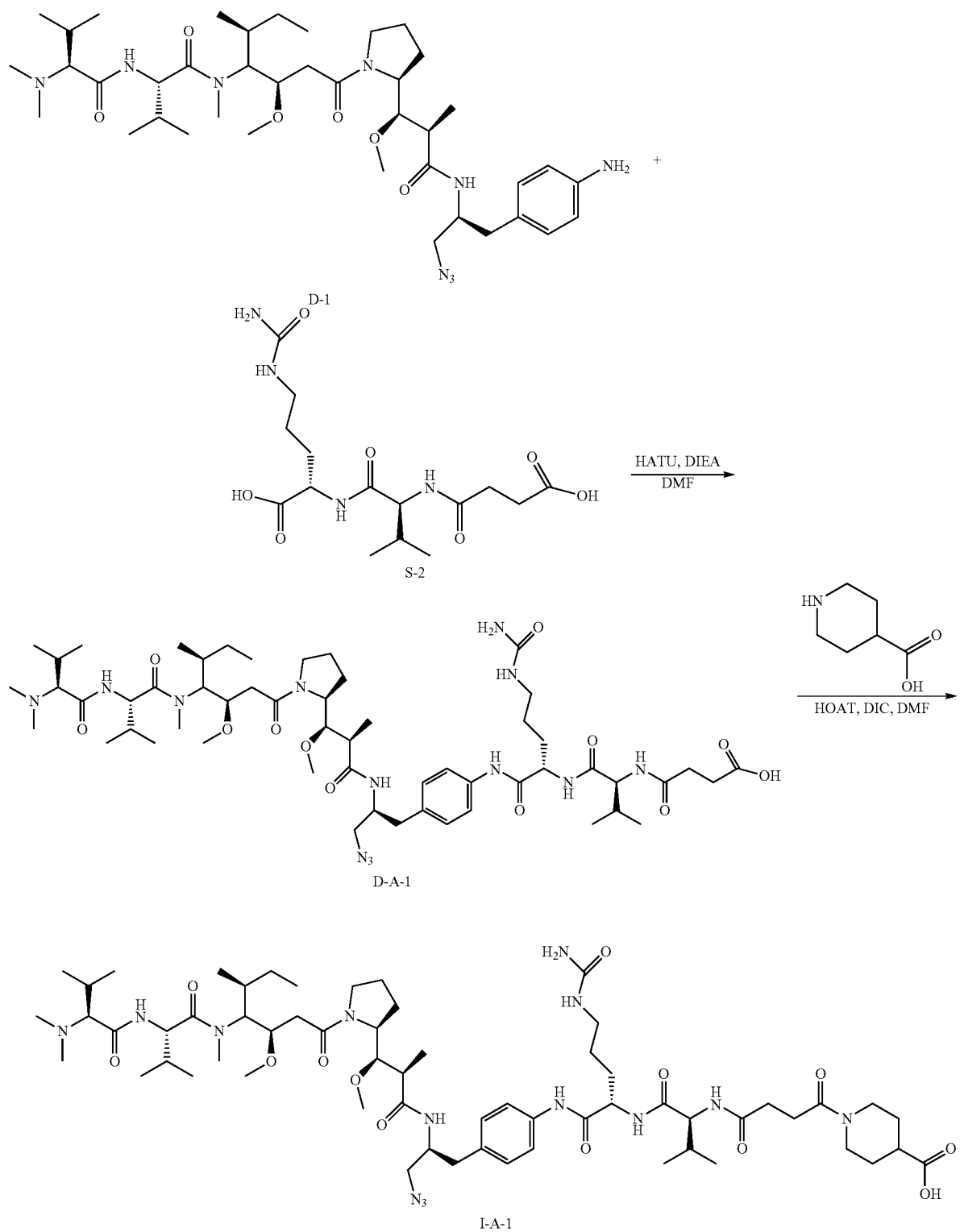

At room temperature, Compound S-2 (0.1 mmol, 1 eq.) was dissolved in DMF (50 ml), and DIEA (2 eq.), HATU (1.05 eq.) and Compound D-1 (2.0 eq.) were added successively. The reaction proceeded for 12 hours at room temperature, and then water (300 ml) and EtOAc (100 ml*3) were added. After extraction, the organic phase was collected, concentrated and purified by HPLC to obtain Intermediate D-A-1.

At room temperature, Compound D-A-1 (0.1 mmol, 1 eq.) was dissolved in DMF (5 ml), and DIC (1.1 eq.), HOAt (1.1 eq.) and piperidine-4-carboxylic acid (1.2 eq.) were added successively. The reaction mixture was stirred for 6 hours at room temperature, and then water (60 ml) and EtOAc (20 ml*3) were added. After extraction, the organic phase was collected, concentrated and purified by HPLC to obtain Intermediate I-A-1.

MS m/z (ESI): 1240 [M+H]$^+$.

Alternatively,

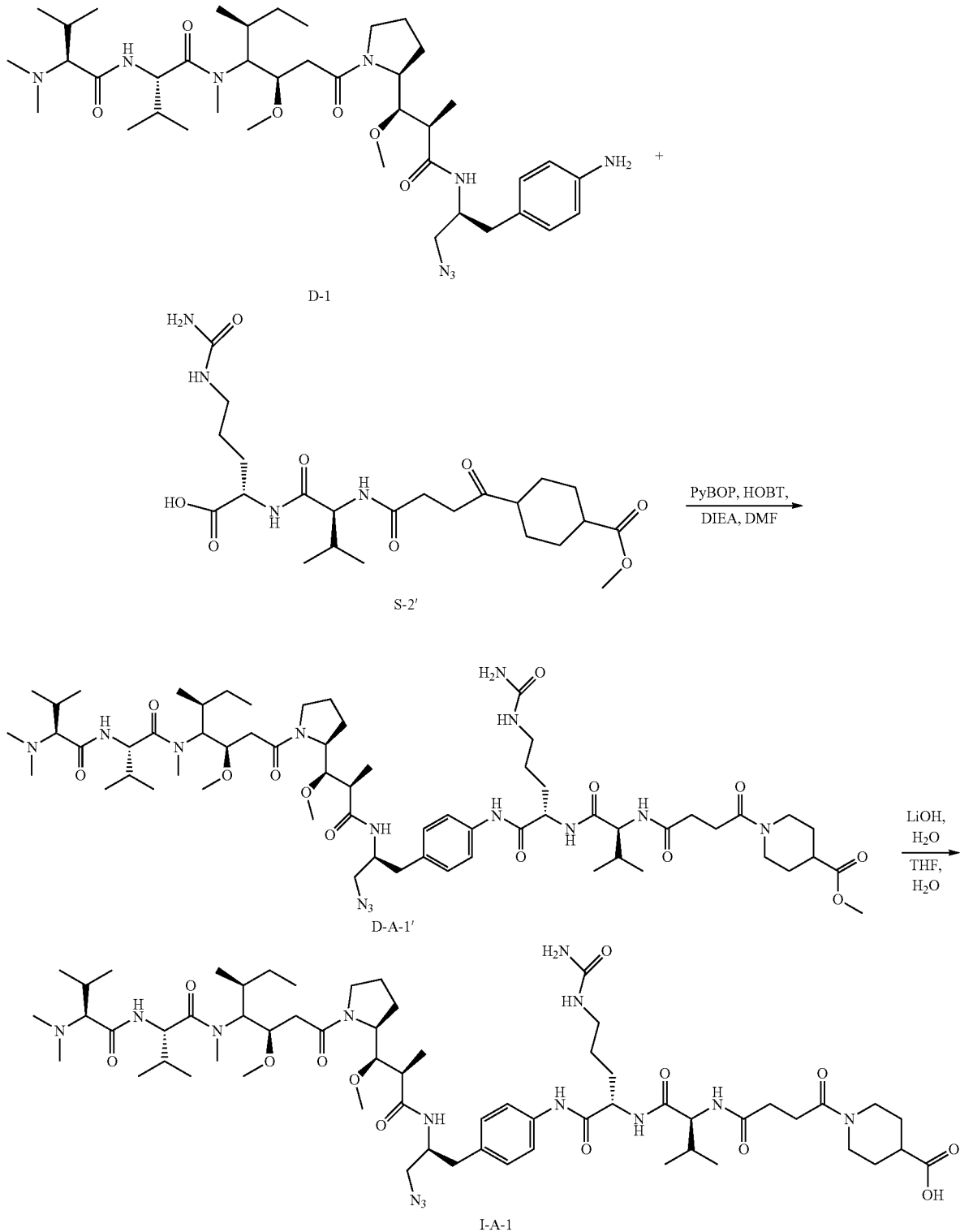

In an ice-water bath, Compound S-2' (0.1 mmol, 1.0 eq.) was dissolved in DMF (10 ml), and DIEA (2.0 eq.), PyBOP (1.0 eq.), HOBT (1.0 eq.) and Compound D-1 (0.2 mmol, 2.0 eq.) were added successively. The reaction proceeded for 12 hours at room temperature, and then water (30 ml) and EtOAc (10 ml*3) were added. After extraction, the organic phase was collected, concentrated and purified by HPLC to obtain Intermediate D-A-1'.

At room temperature, Compound D-A-1' (0.05 mmol, 1.0 eq.) was dissolved in THF/H$_2$O (6 ml, v:v=5:1), and LiOH monohydrate (3.0 eq.) was added. The reaction mixture was stirred for 16 hours at room temperature. After purification, Intermediate I-A-1 was obtained.

MS m/z (ESI): 1240 [M+H]$^+$.

Step c. Preparation of Intermediate I-B-1

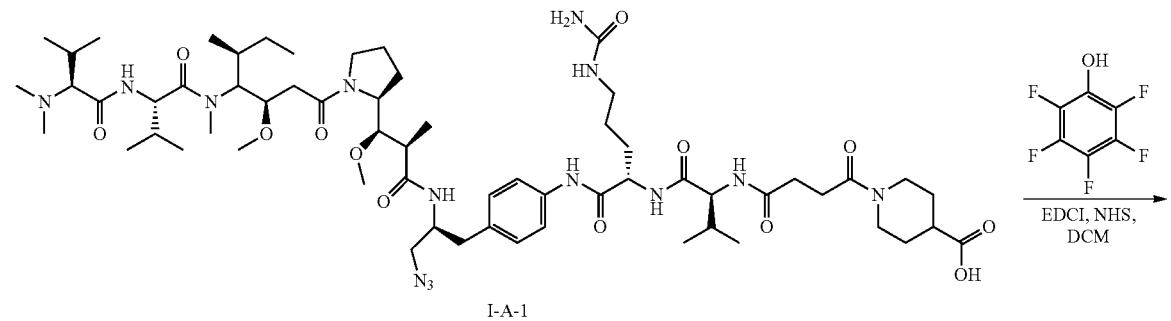

I-A-1

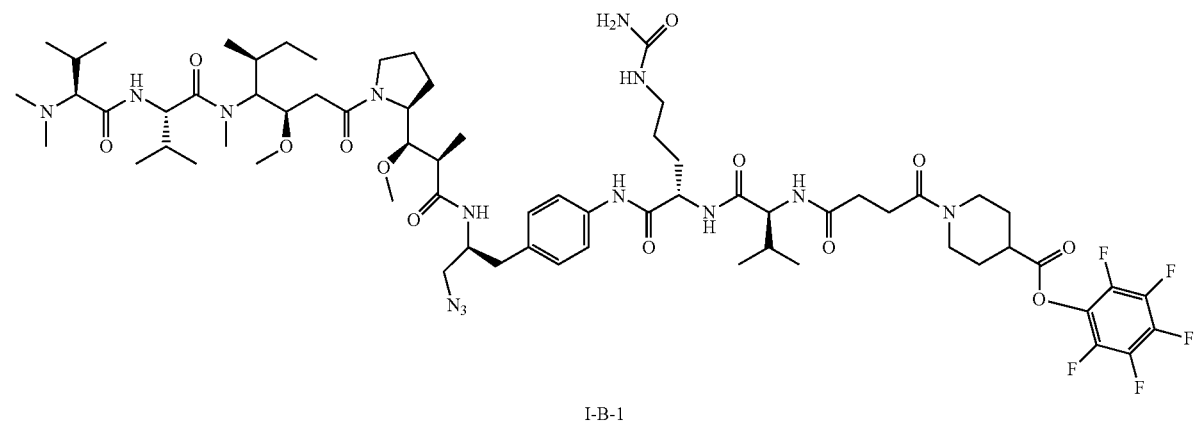

I-B-1

At room temperature, Compound I-A-1 (0.1 mmol, 1 eq.) was dissolved in DCM (50 ml), and EDCI (1.5 eq.), NHS (1.5 eq.) and pentafluorophenol (2.0 eq.) were added successively. The reaction proceeded for 18 hours at room temperature. The reaction mixture was washed successively with water (30 ml), 10% (w/v) citric acid aqueous solution (20 ml) and saturated sodium chloride aqueous solution (20 ml). The organic phase was collected, concentrated and purified by HPLC to obtain Intermediate I-B-1.

MS m/z (ESI): 1406 [M+H]$^+$.

Step d. Preparation of Crude Antibody-Drug Conjugate I-1

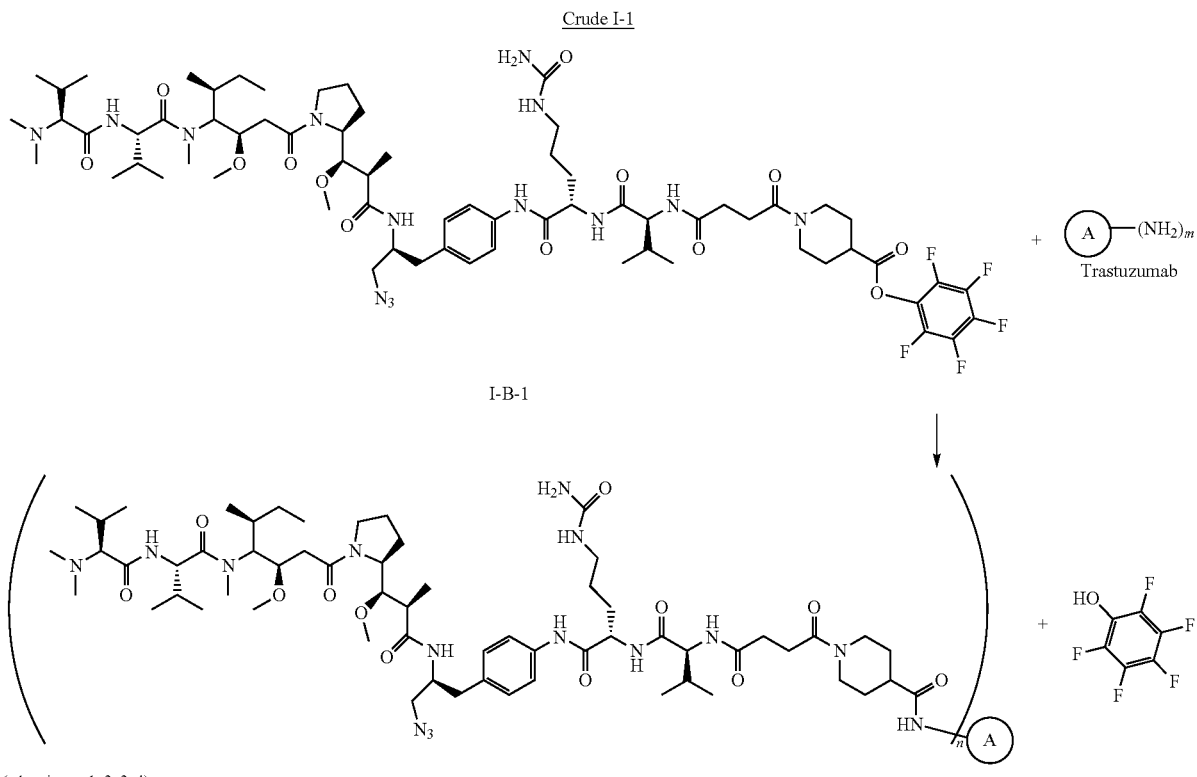

(wherein n = 1, 2, 3, 4)

To 1 ml solution of 10-20 mg/ml of Trastuzumab prepared in PBS buffer (pH=7.4), 4-6 folds molar amount of Compound I-B-1 dissolved in DMA was added. The reaction proceeded under gentle stirring for 2-6 hours at a temperature in the range of 2-40° C., and was monitored by HIC-HPLC, to obtain crude Antibody-Drug Conjugate I-1. The HIC-HPLC chromatogram is shown in FIG. 1.

HIC-HPLC conditions:
Column: Tosoh TSKgel Butyl-NPR, 4.6×100 mm
Mobile phase A: 1.5 M ammonia sulfate aqueous solution
Mobile phase B: 25 mM sodium phosphate aqueous solution, pH=7.0, 25% (v/v) isopropanol aqueous solution
Flow rate: 0.5 ml/min
Gradient: 0-2 min: 17% mobile phase B+83% mobile phase A;
2-15 min: 17-40% mobile phase B+83-60% mobile phase A
15-15.1 min: 40-70% mobile phase B+60-30% mobile phase A
15.1-17 min: 70% mobile phase B+30% mobile phase A It can be seen from FIG. 1 that the crude Antibody-Drug Conjugate I-1 is a mixture comprising I-1-1 (DAR1 in FIG. 1, n=1), I-1-2 (DAR2 in FIG. 1, n=2), I-1-3 (DAR3 in FIGS. 1, n=3), and I-1-4 (DAR4 in FIG. 1, n=4).

Step e. Purification of Crude Antibody-Drug Conjugate I-1

The crude Antibody-Drug Conjugate I-1 obtained in step d was purified by HIC, then desalted by buffer change, and concentrated by ultrafiltration to obtain Antibody-Drug Conjugate I-1.

Figure 2:
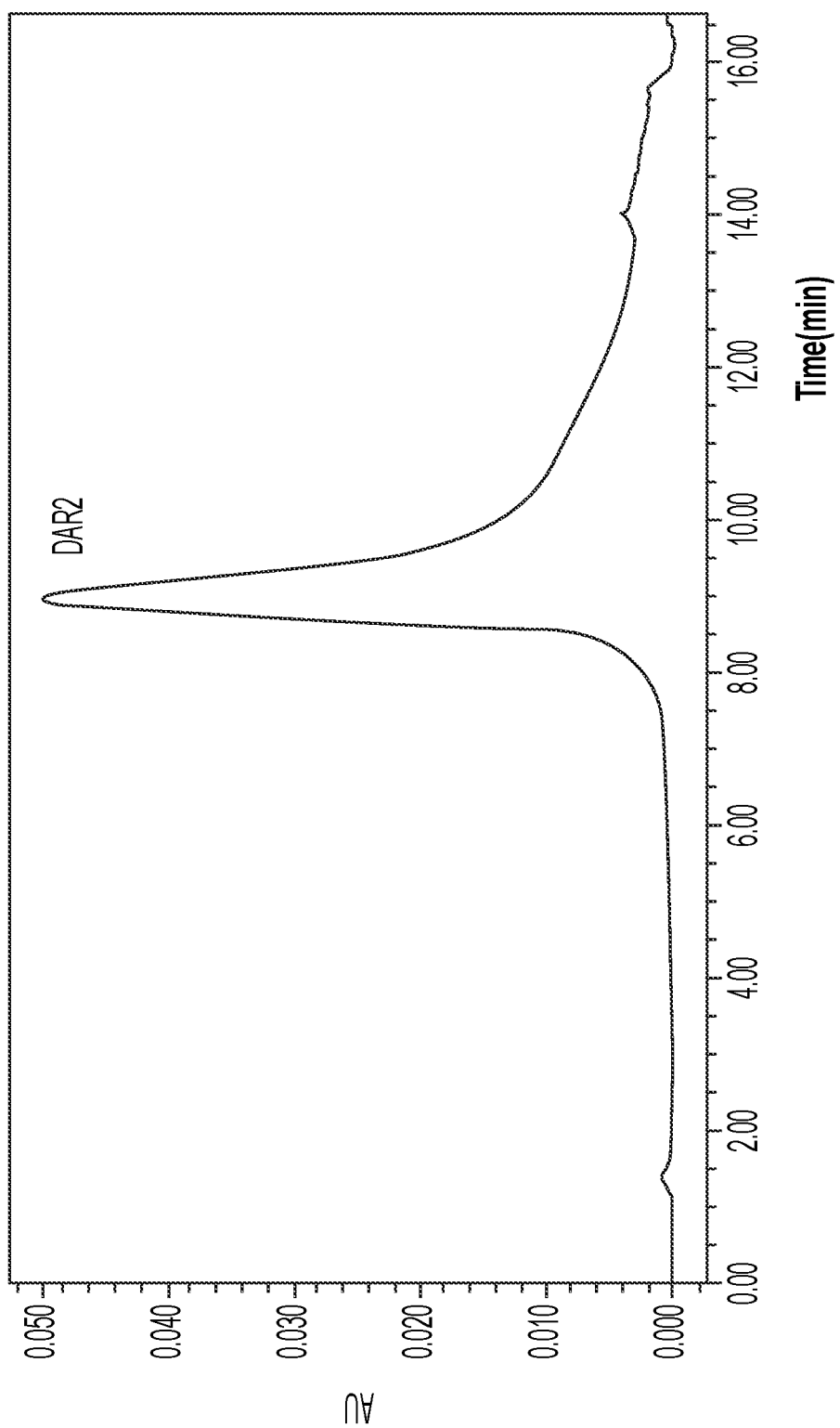
FIG. 2 shows a HIC-UPLC chromatogram of Antibody-Drug Conjugate I-1.

HIC Conditions:
Packing material: Pheynl HP from GE
Mobile phase A: 1.5 M ammonia sulfate aqueous solution, 25 mM disodium hydrogen phosphate aqueous solution, pH=7.0
Mobile phase B: 25 mM disodium hydrogen phosphate aqueous solution, pH=7.0, 10% isopropanol aqueous solution
Flow rate: 1.0 ml/min
Gradient: 0%-40% mobile phase B washing for 20 CV; 40%-100% mobile phase B washing for 30 CV, collected in tubes DAR of the resulting Antibody-Drug Conjugate I-1 was analyzed by HIC-UPLC, and the chromatogram as shown in FIG. 2 was obtained. It can be seen from FIG. 2 that Antibody-Drug Conjugate I-1 showed a single peak, and an analysis with combining the peptide mapping in FIG. 4 indicated that Antibody-Drug Conjugate I-1 has DAR of 2, i.e. n=2. It is an antibody-drug conjugate in which two drug molecules are conjugated to one antibody molecule, and the product is pure.

Figure 3:
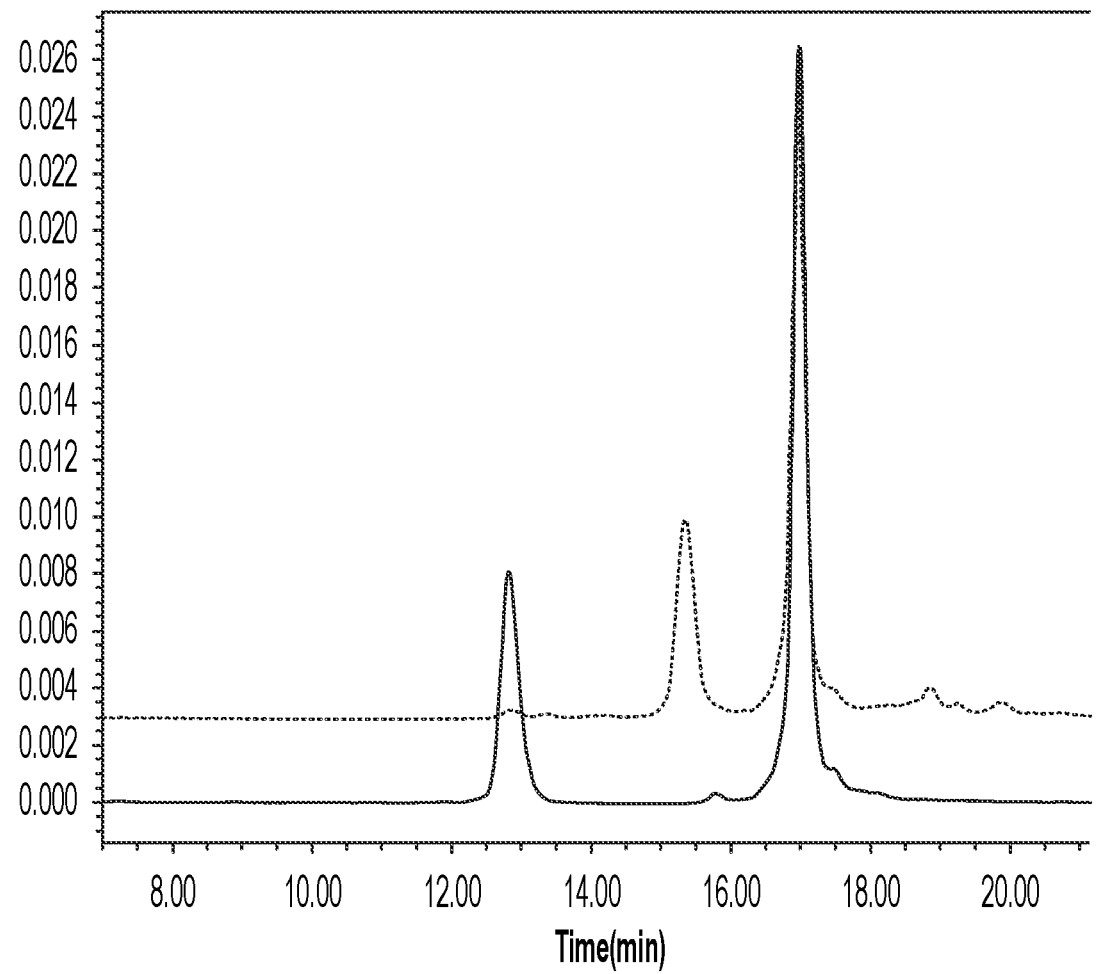
FIG. 3 shows overlapping reduced reverse-phase chromatograms of Antibody-Drug Conjugate I-1 and Trastuzumab.

Furthermore, the heavy and light chains of Antibody-Drug Conjugate I-1 were analyzed by reduced liquid chromatography, and the overlapping reverse-phase chromatogram as shown in FIG. 3 was obtained. In FIG. 3, the dark line represents the chromatogram of Trastuzumab, and the light line represents the chromatogram of Antibody-Drug Conjugate I-1. In both chromatograms, the higher peak represents the heavy chain and the lower peak represents the light chain. It can be seen from FIG. 3 that the hydrophobicity of the light chain of Antibody-Drug Conjugate I-1 is enhanced as compared with that of Trastuzumab without conjugated drugs, showing longer retention time. This indicates that all the drug molecules are conjugated to the light chain of the antibody.

Figure 4:
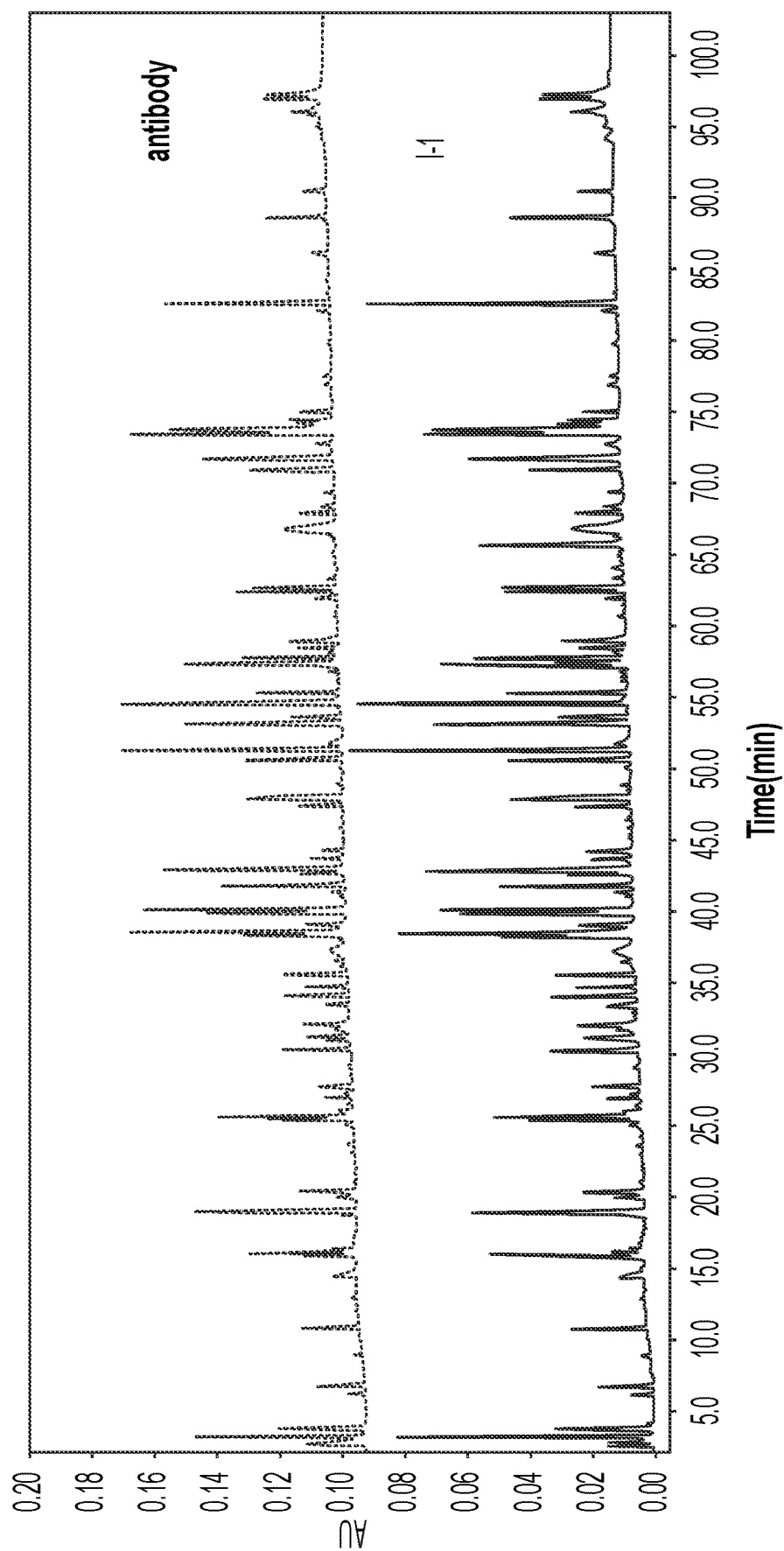
FIG. 4 shows peptide mappings obtained after protease hydrolysis of Antibody-Drug Conjugate I-1 and Trastuzumab under same conditions.

Furthermore, peptide mappings of both Antibody-Drug Conjugate I-1 and Trastuzumab, as shown in FIG. 4, were obtained after digestion under the same conditions.

In the peptide mappings of FIG. 4, the upper curve is the peptide mapping of the antibody at 214 nm, and the lower one is that of Antibody-Drug Conjugate I-1. Comparison shows that Antibody-Drug Conjugate I-1 has only one additional peak at the retention time of 65.5 min. With the reduced chromatograms of the light and heavy chains in FIG. 3, the cytotoxic agents (D) are all conjugated to the lysine residues of the same peptide segment of the light chain in Antibody-Drug Conjugate I-1 obtained in this example, and site specific conjugation assures excellent homogeneity, controllability, and repeatability of the product.

Example 2. Preparation of Antibody-Drug Conjugate I-2

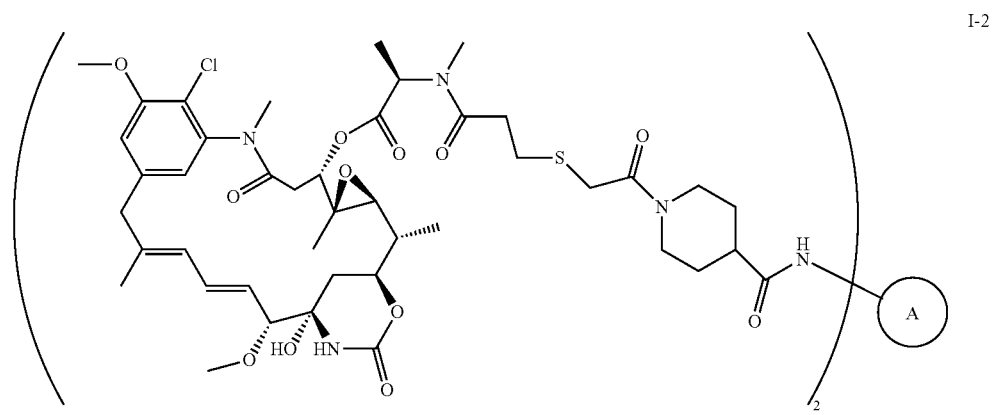

I-2

Step a. Preparation of Intermediate I-A-2

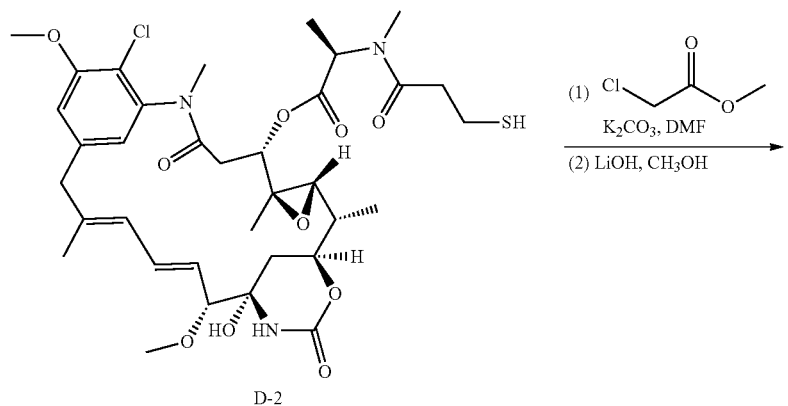

D-2

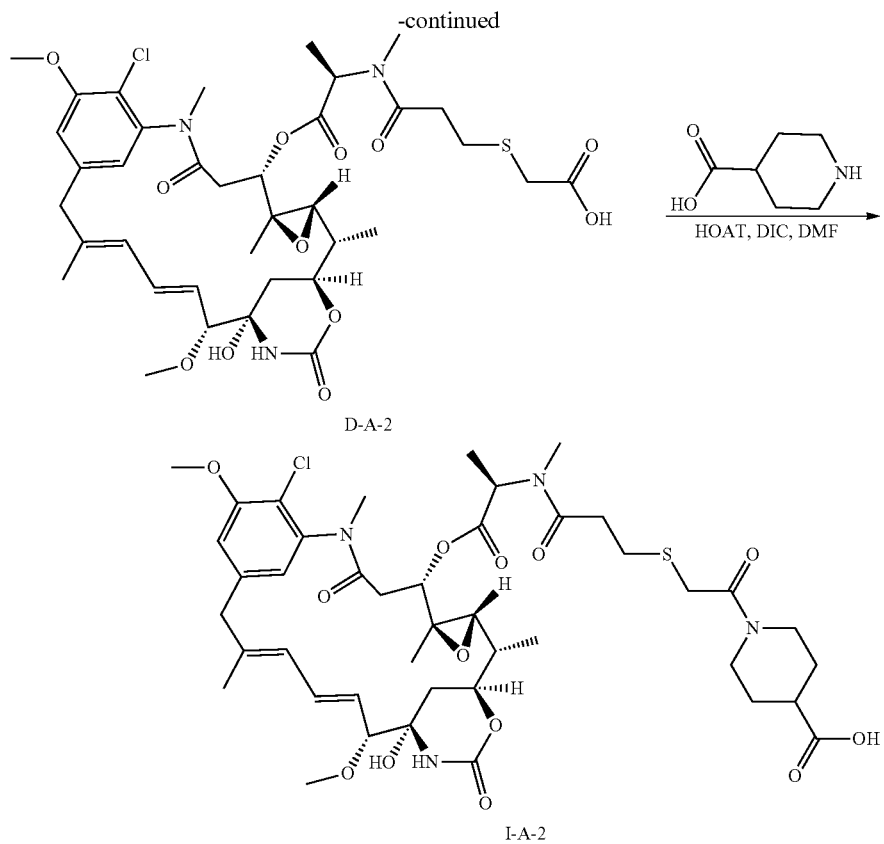

At room temperature, Compound D-2 (purchased from Nanjing Levena Biopharma Co., Ltd., 1 mmol, 1 eq.) was dissolved in DMF (50 ml), and potassium carbonate (2.5 eq.) and methyl 2-chloroacetate (1.5 eq.) were added. The reaction mixture was heated to 40-45° C., and the reaction proceeded for 4 hours. After completion of the reaction, the solid potassium carbonate was removed by filtration, and the filtrate was concentrated. The substance resulting from concentration was dissolved in methanol (30 ml), and 1 M lithium hydroxide aqueous solution was added to adjust the pH to 13-14. The reaction mixture was heated to 55° C., and stirred for 16 hours, followed by addition of 10% (w/v) citric acid aqueous solution, concentration and purification by HPLC to obtain Intermediate D-A-2.

At room temperature, Compound D-A-2 (0.1 mmol, 1 eq.) was dissolved in DMF (5 ml), and DIC (1.1 eq.), HOAt (1.1 eq.) and piperidine-4-carboxylic acid (1.2 eq.) were added successively. The reaction mixture was stirred for 6 hours at room temperature, and then water (60 ml) and EtOAc (20 ml*3) were added. After extraction, the organic phase was collected, concentrated and purified by HPLC to obtain Intermediate I-A-2.

MS m/z (ESI): 907 [M+H]$^+$.

Step b. Preparation of Intermediate I-B-2

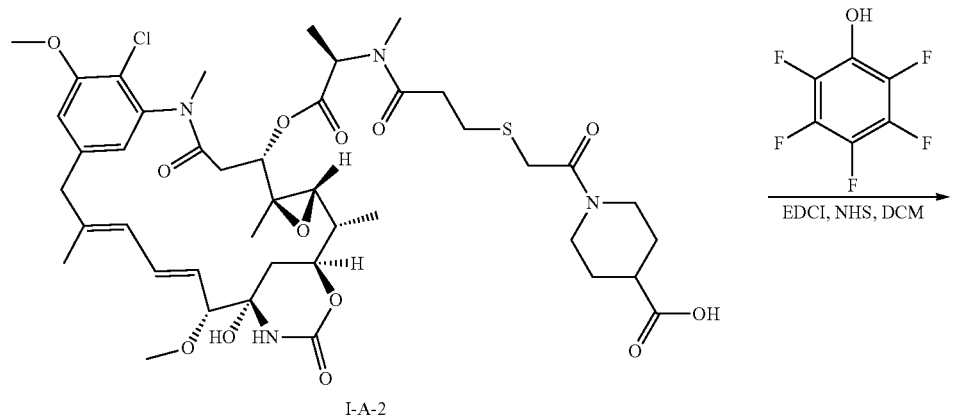

-continued

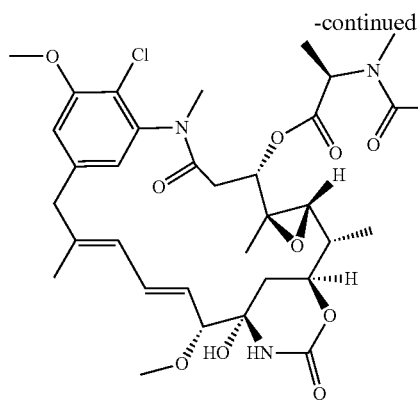
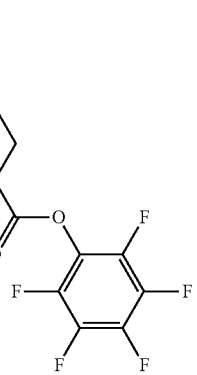

I-B-2

At room temperature, Compound I-A-2 (0.1 mmol, 1 eq.) was dissolved in DCM (50 ml), and EDCI (1.5 eq.), NHS (1.5 eq.) and pentafluorophenol (2.0 eq.) were added successively. The reaction proceeded for 18 hours at room temperature. The reaction mixture was washed successively with water (30 ml), saturated citric acid aqueous solution (20 ml) and saturated sodium chloride aqueous solution (20 ml). After extraction, the organic phase was collected, concentrated and purified by HPLC to obtain Intermediate I-B-2.

MS m/z (ESI): 1073 [M+H]$^+$.

Step c. Preparation of Crude Antibody-Drug Conjugate I-2

Crude I-2

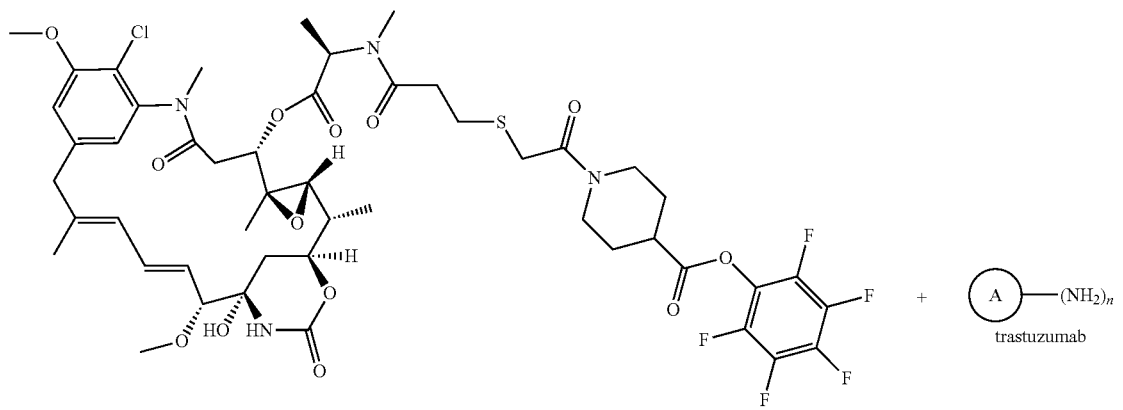

I-B-2

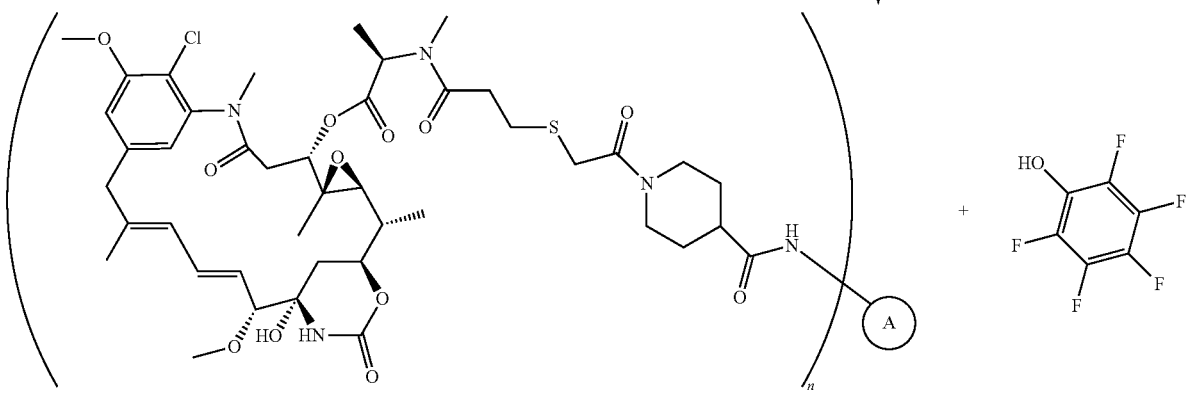

(wherein n = 1, 2, 3)

To 1 ml solution of 10 mg/ml of Trastuzumab prepared in PBS buffer (pH=7.4), 8 folds molar amount of Compound I-B-2 dissolved in DMA was added. The reaction proceeded under gentle stirring for 16 hours at room temperature, and was monitored by HIC-HPLC (HIC-HPLC conditions were the same as those in step d of Example 1), to obtain crude Antibody-Drug Conjugate I-2. The HIC-HPLC chromatogram is shown in FIG. 5.

Figure 5:
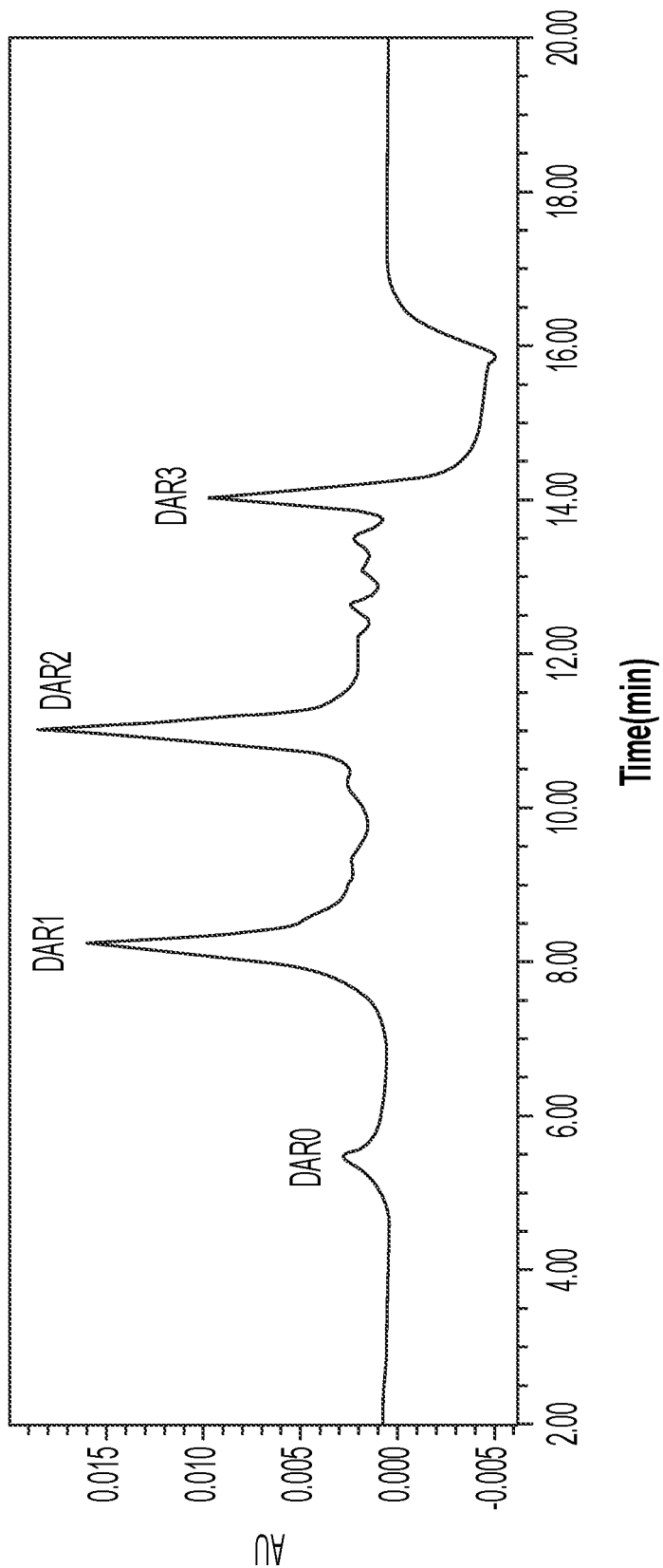
FIG. 5 shows a HIC-HPLC chromatogram of crude Antibody-Drug Conjugate I-2.

It can be seen from FIG. 5 that the crude Antibody-Drug Conjugate I-2 is a mixture comprising I-2-1 (DAR1 in FIG. 5, n=1), I-2-2 (DAR2 in FIGS. 5, n=2), and I-2-3 (DAR3 in FIG. 5, n=3).

Step d. Purification of Crude Antibody-Drug Conjugate I-2

The crude Antibody-Drug Conjugate I-2 obtained in step c was purified by HIC (HIC conditions were the same as those in step e of Example 1), then desalted by buffer change, and concentrated by ultrafiltration to obtain Antibody-Drug Conjugate I-2.

Figure 6:
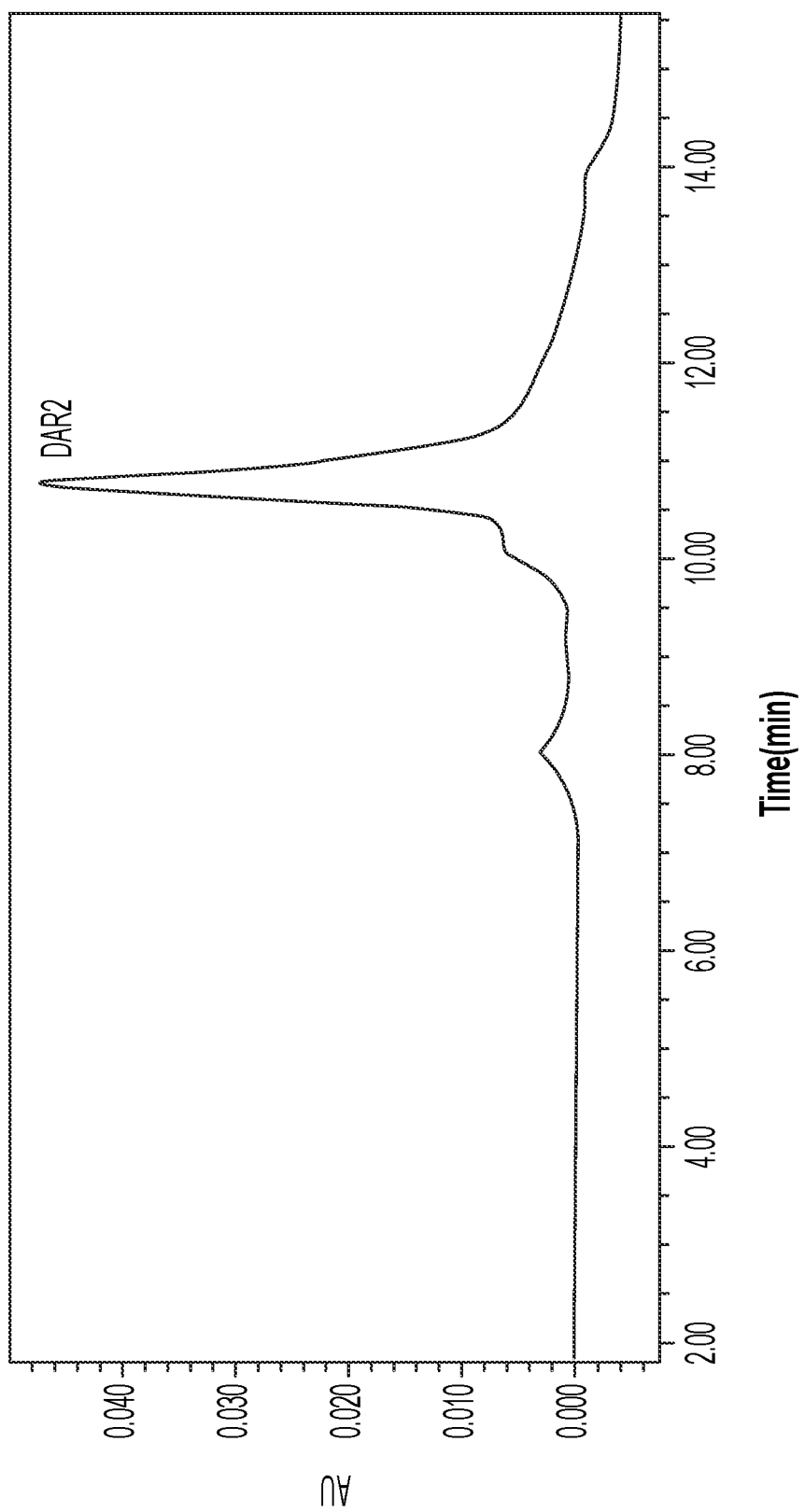
FIG. 6 shows a HIC-HPLC chromatogram of Antibody-Drug Conjugate I-2.

DAR of the resulting Antibody-Drug Conjugate I-2 was analyzed by HIC-HPLC, and the chromatogram as shown in FIG. 6 was obtained. It can be seen from FIG. 6 that the DAR of Antibody-Drug Conjugate I-2 is 2, indicating n=2 in the antibody-drug conjugate. It is an antibody-drug conjugate in which two drug molecules are conjugated to one antibody molecule, and the product is pure.

Figure 7:
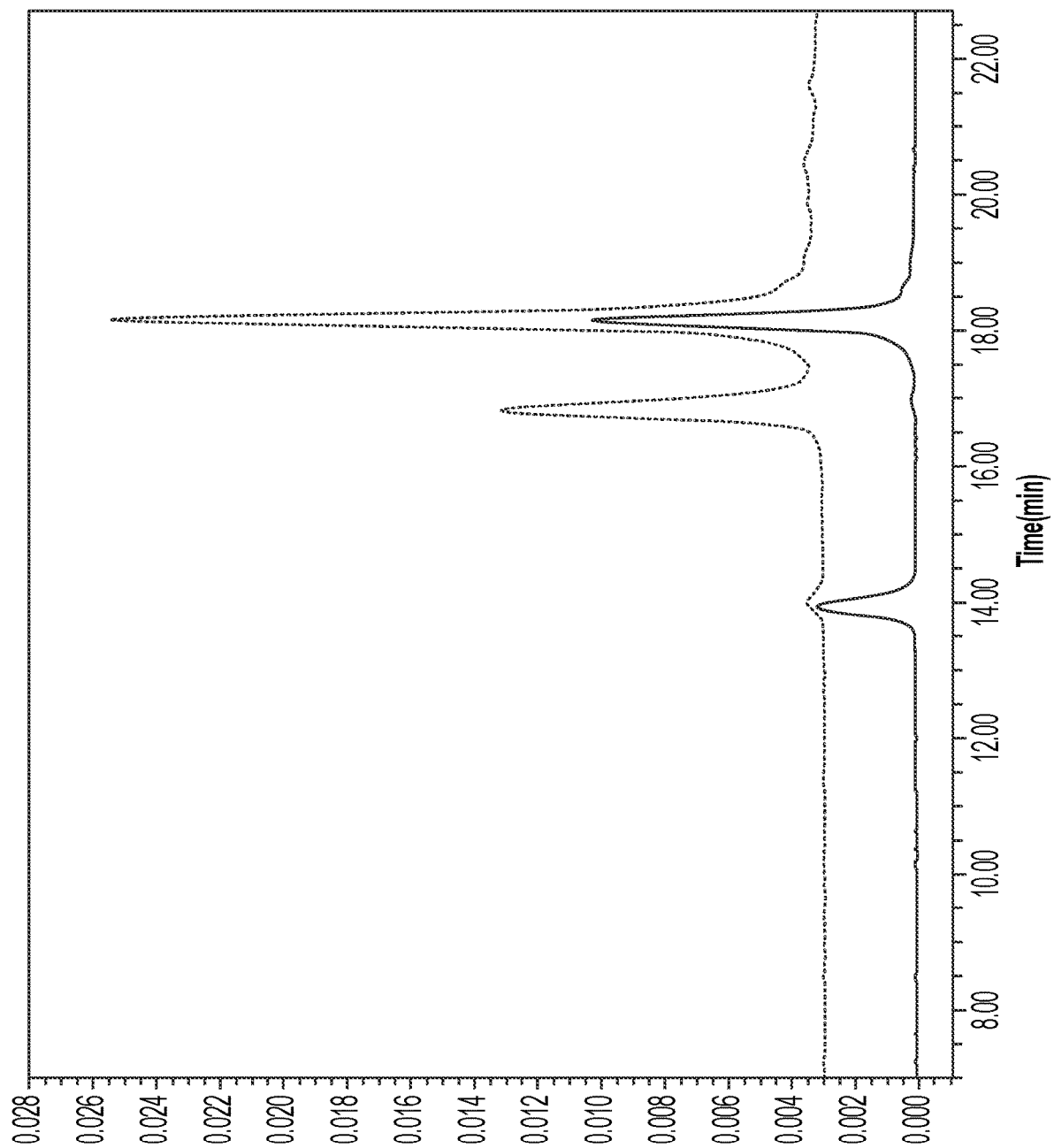
FIG. 7 shows overlapping reduced reverse-phase chromatograms of Antibody-Drug Conjugate I-2 and Trastuzumab.

Furthermore, the heavy and light chains of Antibody-Drug Conjugate I-2 were analyzed by reduced liquid chromatography, and the overlapping chromatogram as shown in FIG. 7 was obtained. In FIG. 7, the dark line represents the chromatogram of Trastuzumab, and the light line represents the chromatogram of Antibody-Drug Conjugate I-2. In both chromatograms, the higher peak represents the heavy chain and the lower peak represents the light chain. It can be seen from FIG. 7 that the hydrophobicity of the light chain of Antibody-Drug Conjugate I-2 is enhanced as compared with that of Trastuzumab without conjugated drugs, showing longer retention time. This indicates that all the drug molecules are conjugated to the light chain of the antibody.

Figure 8:
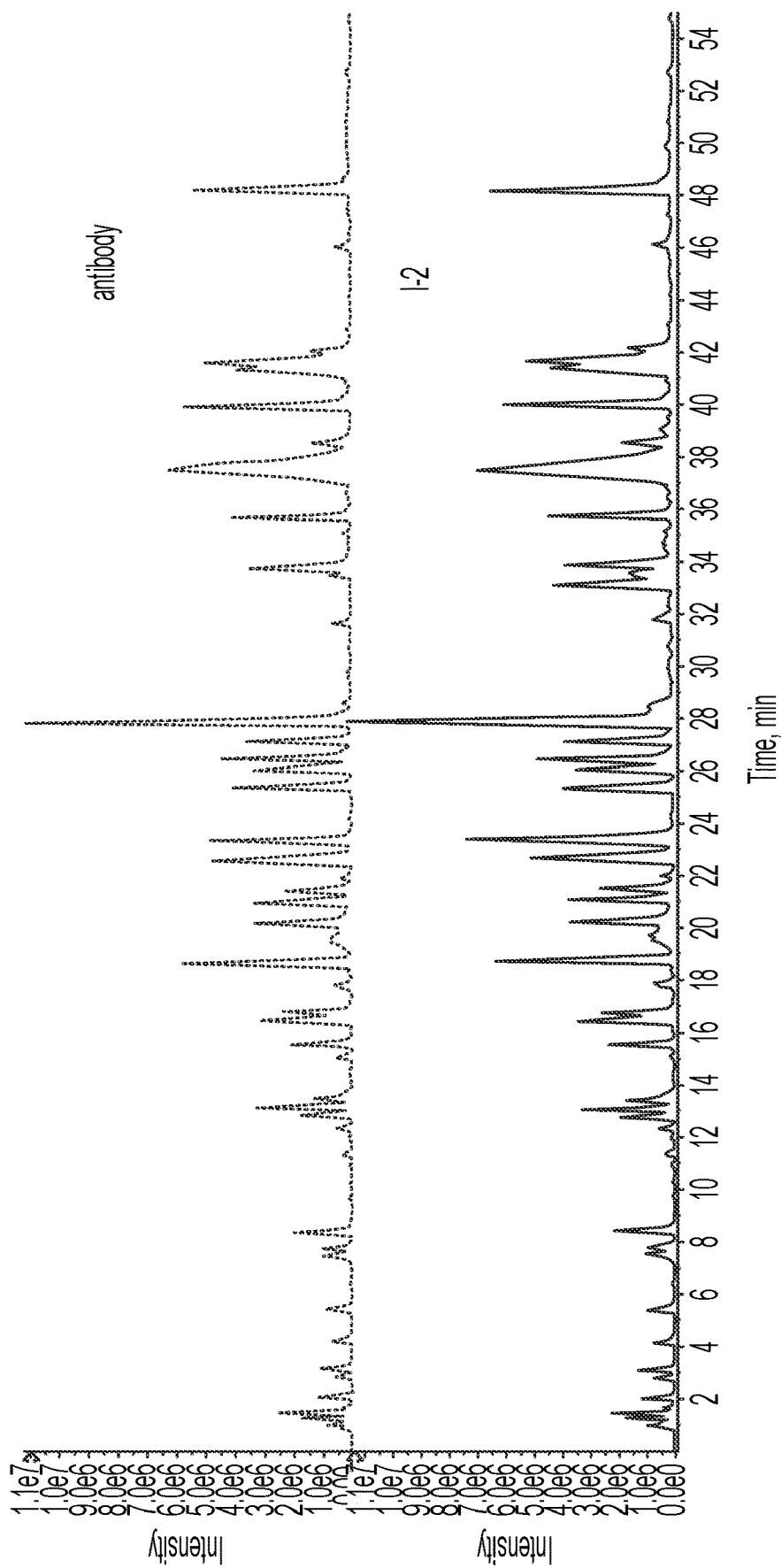
FIG. 8 shows peptide mappings obtained after protease hydrolysis of Antibody-Drug Conjugate I-2 and Trastuzumab under same conditions.

Furthermore, peptide mappings of both Antibody-Drug Conjugate I-2 and Trastuzumab, as shown in FIG. 8, were obtained after digestion under the same conditions.

In the peptide mappings of FIG. 8, the upper curve is the peptide mapping of the antibody at 214 nm, and the lower one is that of Antibody-Drug Conjugate I-2. Comparison shows that Antibody-Drug Conjugate I-2 has only one additional peak at the retention time of 33.0 min. With the reduced chromatograms of the light and heavy chains in FIG. 7, the cytotoxic agents (D) are all conjugated to the lysine residues of the same peptide segment of the light chain in Antibody-Drug Conjugate I-2 obtained in this example, and site specific conjugation assures excellent homogeneity, controllability, and repeatability of the product.

Example 3. Preparation of Antibody-Drug Conjugate I-3

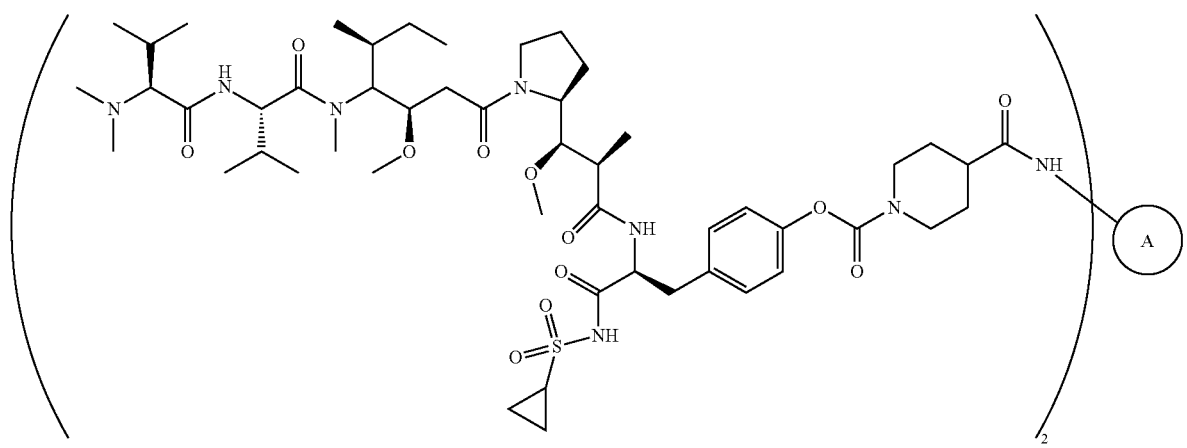

I-3

Step a. Preparation of Intermediate I-A-3

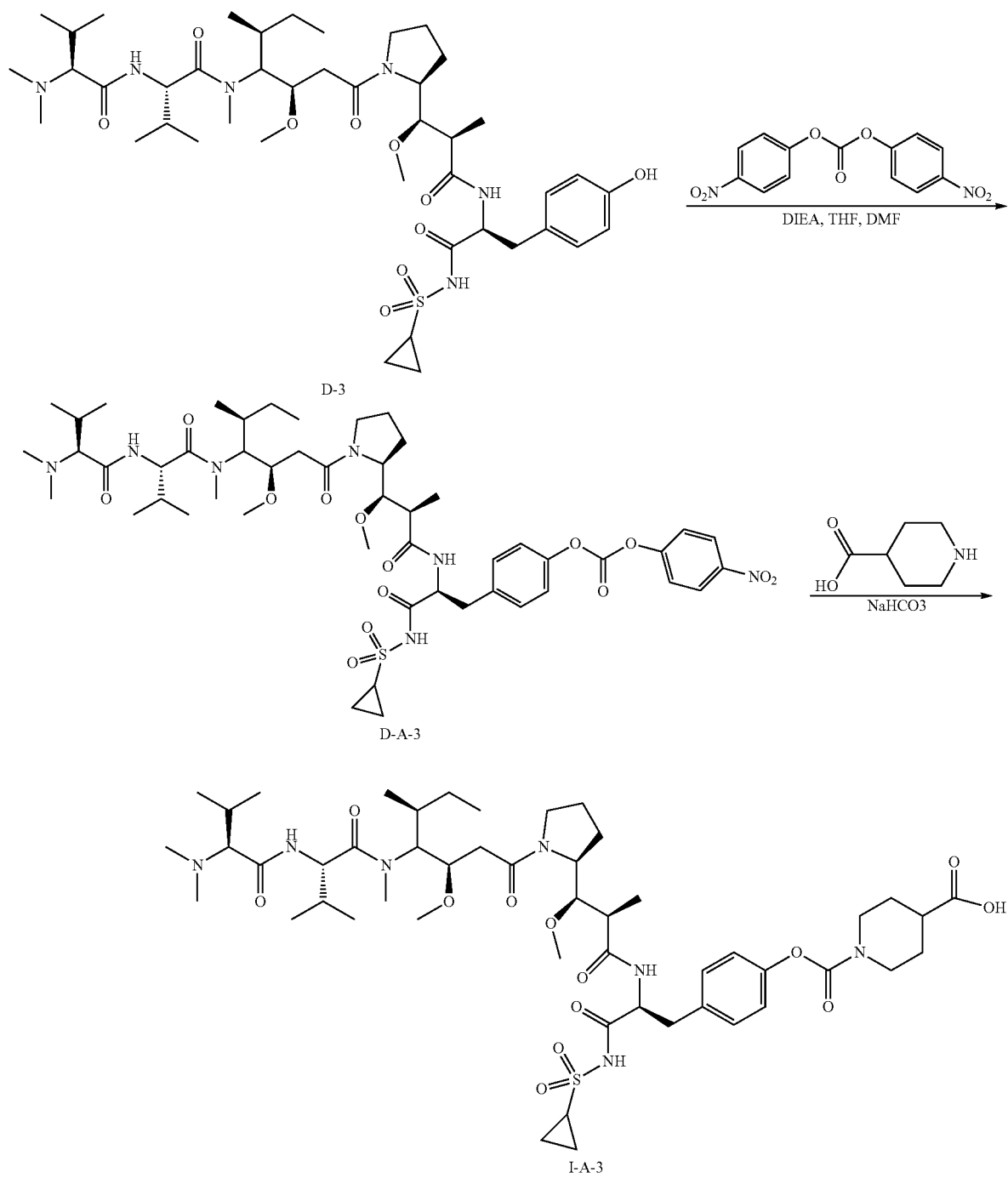

At room temperature, Compound D-3 (synthetized according to Example V-3 at page 65 of CN 104662000A, 1 mmol, 1 eq.) was dissolved in a mixture of THF (60 ml) and DMF (30 ml), and di-(p-nitrophenyl)carbonate (3 eq.) and DIEA (2 eq.) were added successively. The reaction mixture was stirred for 12 hours at room temperature, and water (600 ml) and EtOAc (200 ml*3) were added. After extraction, the organic phase was collected and concentrated to obtain crude Intermediate D-A-3 which was used directly for the reaction in the next step without purification.

At room temperature, piperidine-4-carboxylic acid (5 eq.) was dissolved in saturated NaHCO$_3$ aqueous solution (5 ml), and crude D-A-3 (1 eq.) was added. The reaction mixture was stirred for 8 hours at room temperature. 10% (w/v) citric acid aqueous solution was added to adjust the pH to 4-5, followed by extraction with EtOAc (150 ml*2). The organic phase was dried and concentrated to obtain the crude Intermediate I-A-3.

MS m/z (ESI):1020 [M+H]$^+$.

Step b. Preparation of Intermediate I-B-3

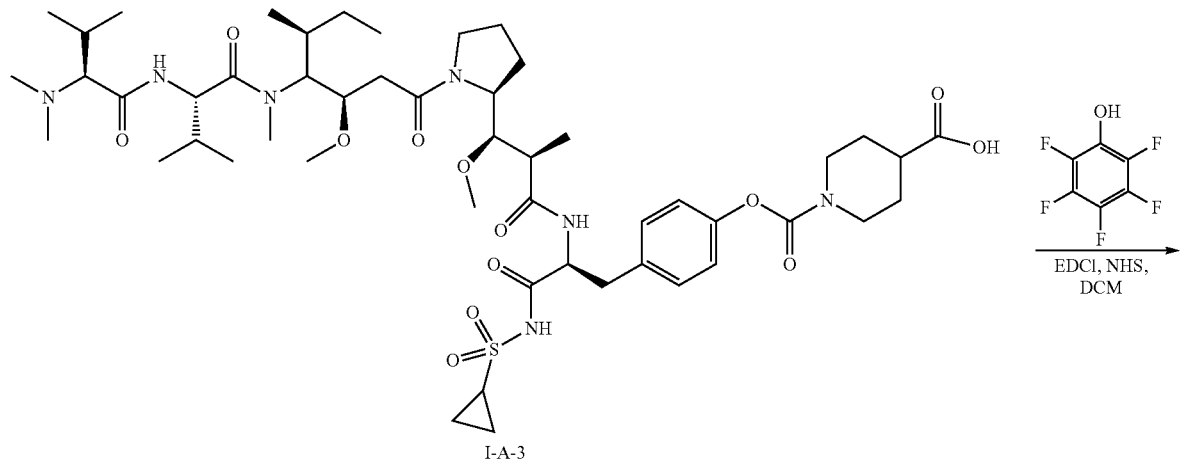

I-A-3

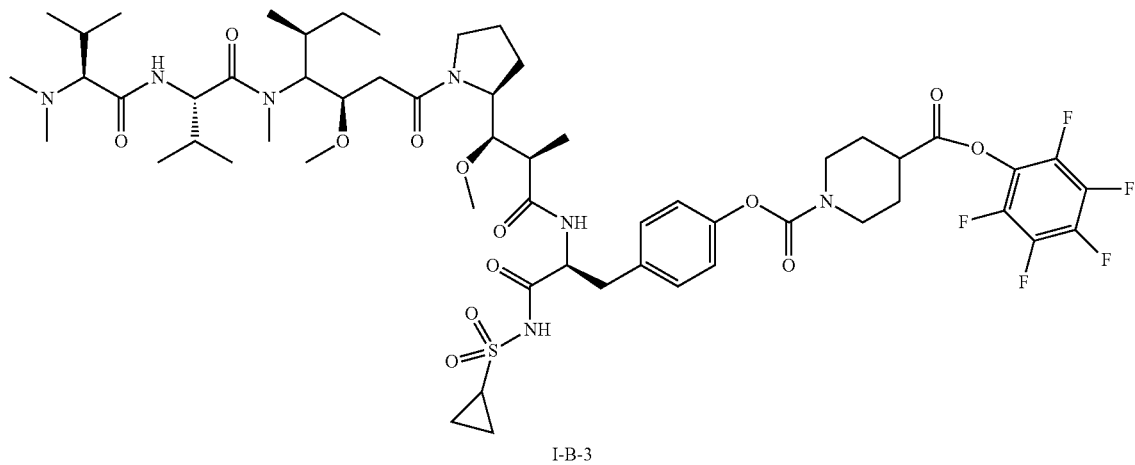

I-B-3

At room temperature, Compound I-A-3 (0.1 mmol, 1 eq.) was dissolved in DCM (50 ml), and EDCI (1.5 eq.), NHS (1.5 eq.) and pentafluorophenol (2.0 eq.) were added successively. The reaction proceeded for 18 hours at room temperature. The reaction mixture was washed successively with water (30 ml), 10% (w/v) citric acid aqueous solution (20 ml) and saturated sodium chloride aqueous solution (20 ml). After extraction, the organic phase was collected, concentrated and purified by HPLC to obtain Intermediate I-B-3.

MS m/z (ESI): 1186 [M+]$^+$.

$^1$H NMR (400 MHz, DMSO-d6) δ: 7.02-7.09 (m, 4H), 4.92 (m, 1H), 4.52 (m, 1H), 3.89 (d, 1H), 3.77 (m, 1H), 3.68-3.55 (m, 3H), 3.46 (m, 2H), 3.24 (m, 6H), 3.05 (d, 2H), 2.92-2.90 (m, 4H), 2.68 (m, 1H), 2.33-2.27 (m, 11H), 1.97-1.93 (m, 4H), 1.73-1.72 (m, 5H), 1.29-1.24 (m, 5H), 1.06-1.01 (m, 15H), 0.96 (m, 3H), 0.74 (m, 4H), 3.34 (m, 4H).

Step c. Preparation of Crude Antibody-Drug Conjugate I-3

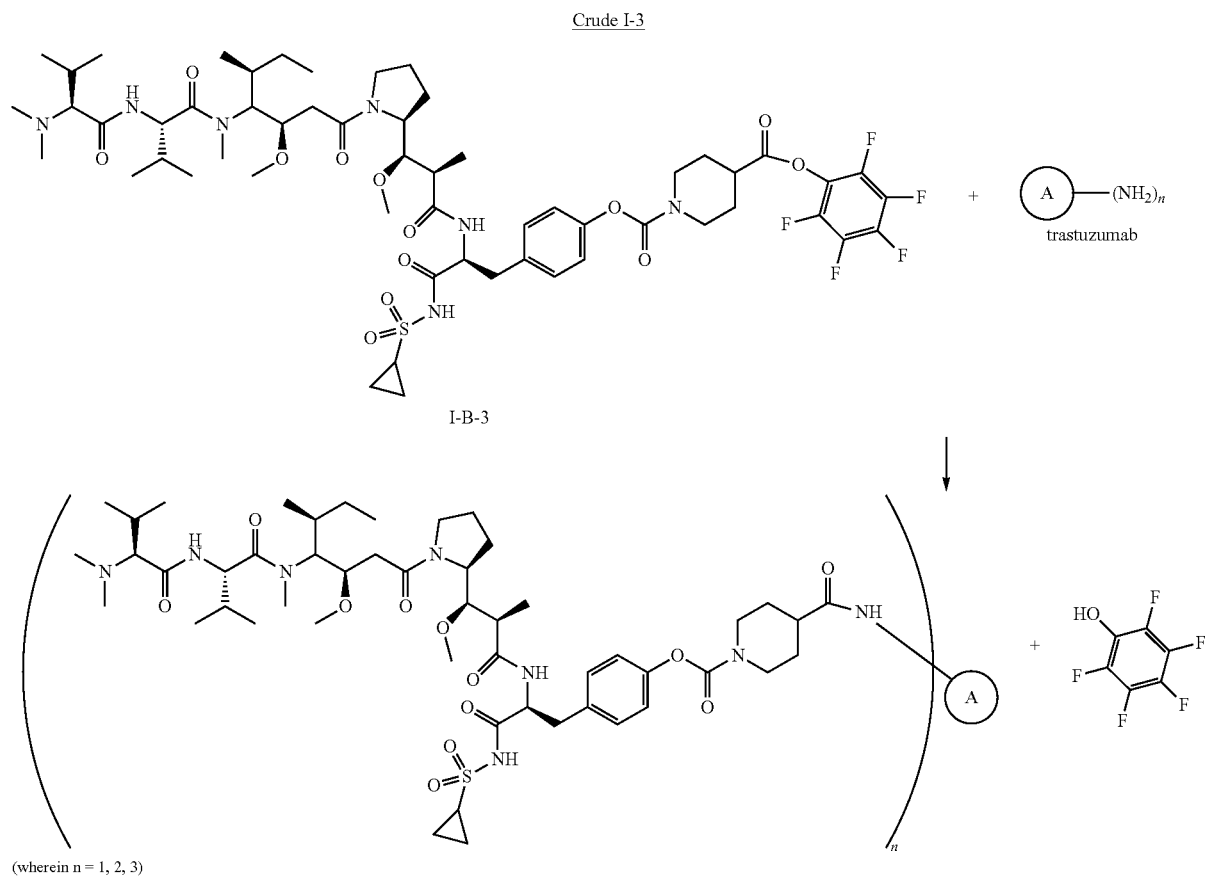

(wherein n = 1, 2, 3)

To 1 ml solution of 10 mg/ml of Trastuzumab prepared in PBS buffer (pH=7.8), 8 folds molar amount of Compound I-B-3 dissolved in DMA was added. The reaction proceeded under gentle stirring for 4 hours at room temperature, and was monitored by HIC-HPLC (HIC-HPLC conditions were the same as those in step d of Example 1), to obtain crude Antibody-Drug Conjugate I-3. The HIC-HPLC chromatogram is shown in FIG. 9.

Figure 9:
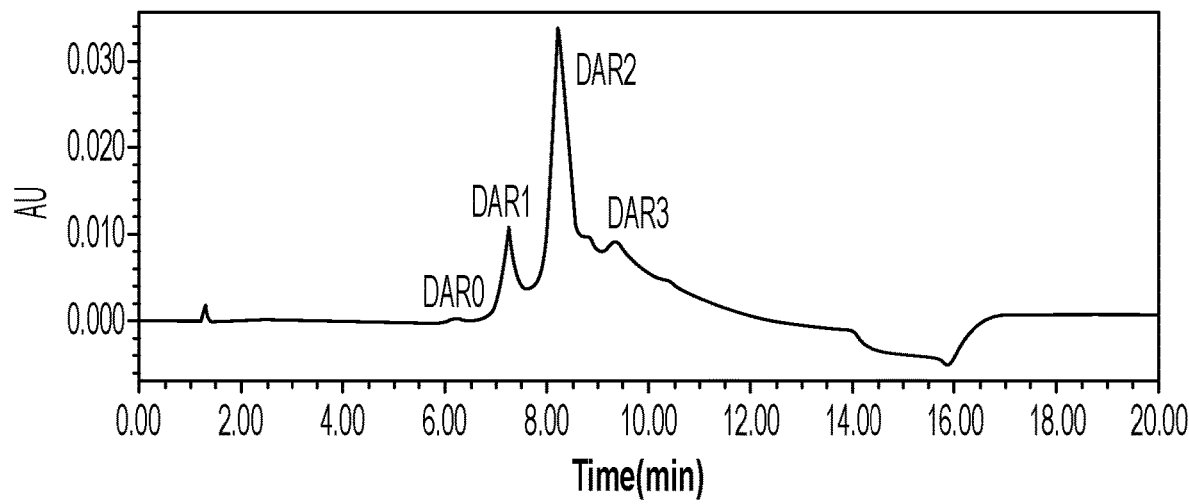
FIG. 9 shows a HIC-HPLC chromatogram of crude Antibody-Drug Conjugate I-3.

It can be seen from FIG. 9 that the crude Antibody-Drug Conjugate I-3 is a mixture comprising I-3-1 (DAR1 in FIG. 9, n=1), I-3-2 (DAR2 in FIGS. 9, n=2), and I-3-3 (DAR3 in FIG. 9, n=3).

Step d. Purification of Crude Antibody-Drug Conjugate I-3

The crude Antibody-Drug Conjugate I-3 obtained in step c was purified by HIC (HIC conditions were the same as those in step e of Example 1), then desalted by buffer change, and concentrated by ultrafiltration to obtain Antibody-Drug Conjugate I-3.

Figure 10:
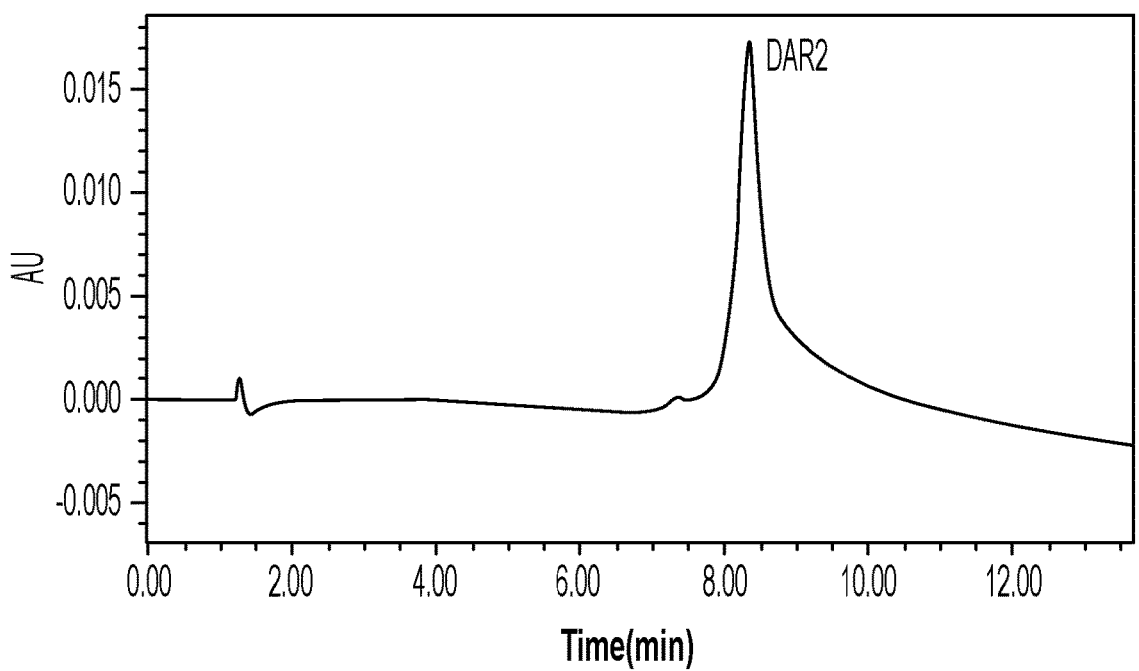
FIG. 10 shows a HIC-HPLC chromatogram of Antibody-Drug Conjugate I-3.

DAR of the resulting Antibody-Drug Conjugate I-3 was analyzed by HIC-HPLC, and the chromatogram as shown in FIG. 10 was obtained. It can be seen from FIG. 10 that the DAR of Antibody-Drug Conjugate I-3 is 2, indicating n=2 in the antibody-drug conjugate. It is an antibody-drug conjugate in which two drug molecules are conjugated to one antibody molecule, and the product is pure.

Figure 11:
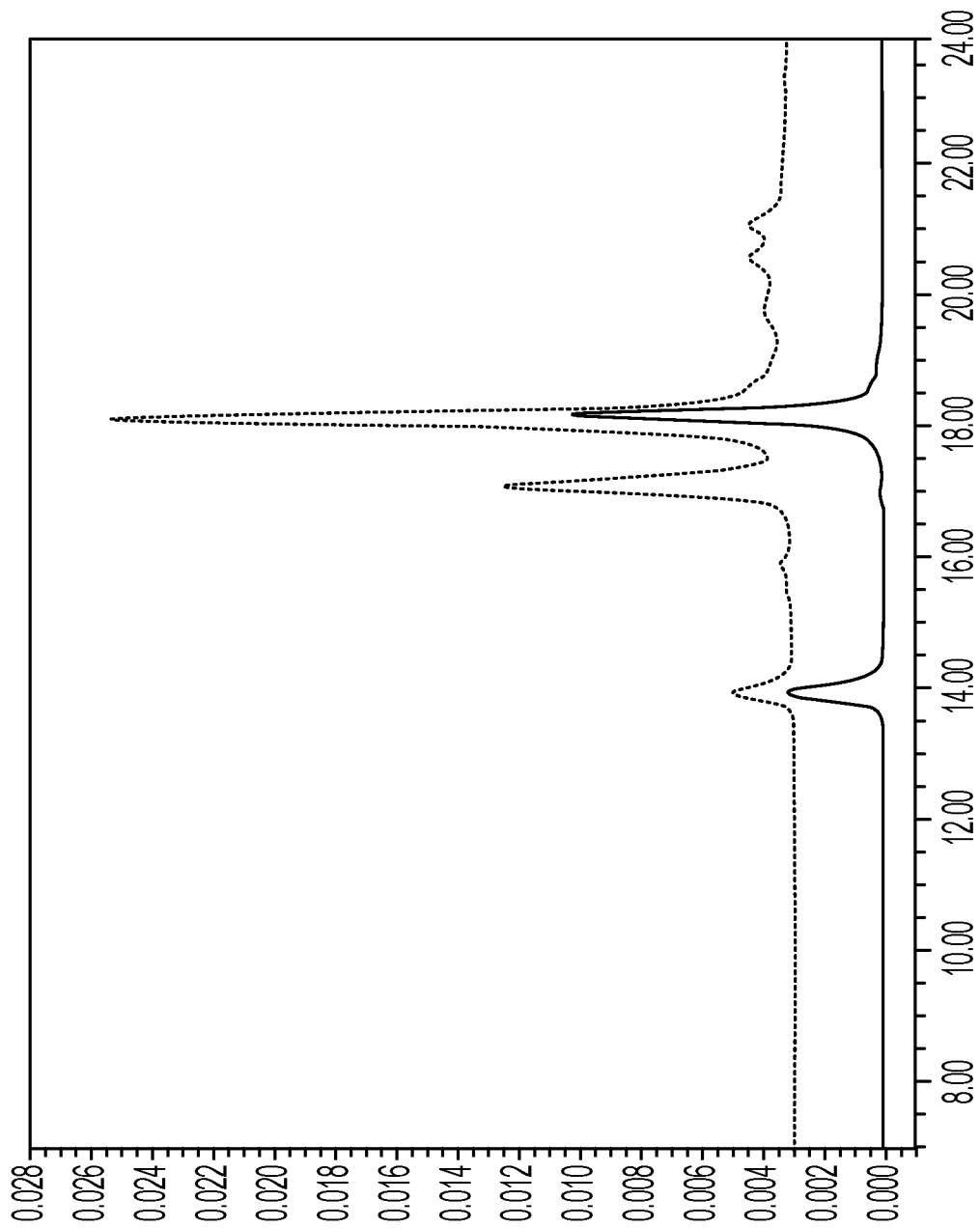
FIG. 11 shows overlapping reduced reverse-phase chromatogram of Antibody-Drug Conjugate I-3 and Trastuzumab.

Furthermore, the heavy and light chains of Antibody-Drug Conjugate I-3 were analyzed by reduced liquid chromatography, and the overlapping chromatogram as shown in FIG. 11 was obtained. In FIG. 11, the dark line represents the chromatogram of Trastuzumab, and the light line represents the chromatogram of Antibody-Drug Conjugate I-3. In both chromatograms, the higher peak represents the heavy chain and the lower peak represents the light chain. It can be seen from FIG. 11 that the hydrophobicity of the light chain of Antibody-Drug Conjugate I-3 is enhanced as compared with that of Trastuzumab without conjugated drugs, showing longer retention time. This indicates that all drug molecules are conjugated to the light chain of the antibody.

Figure 12:
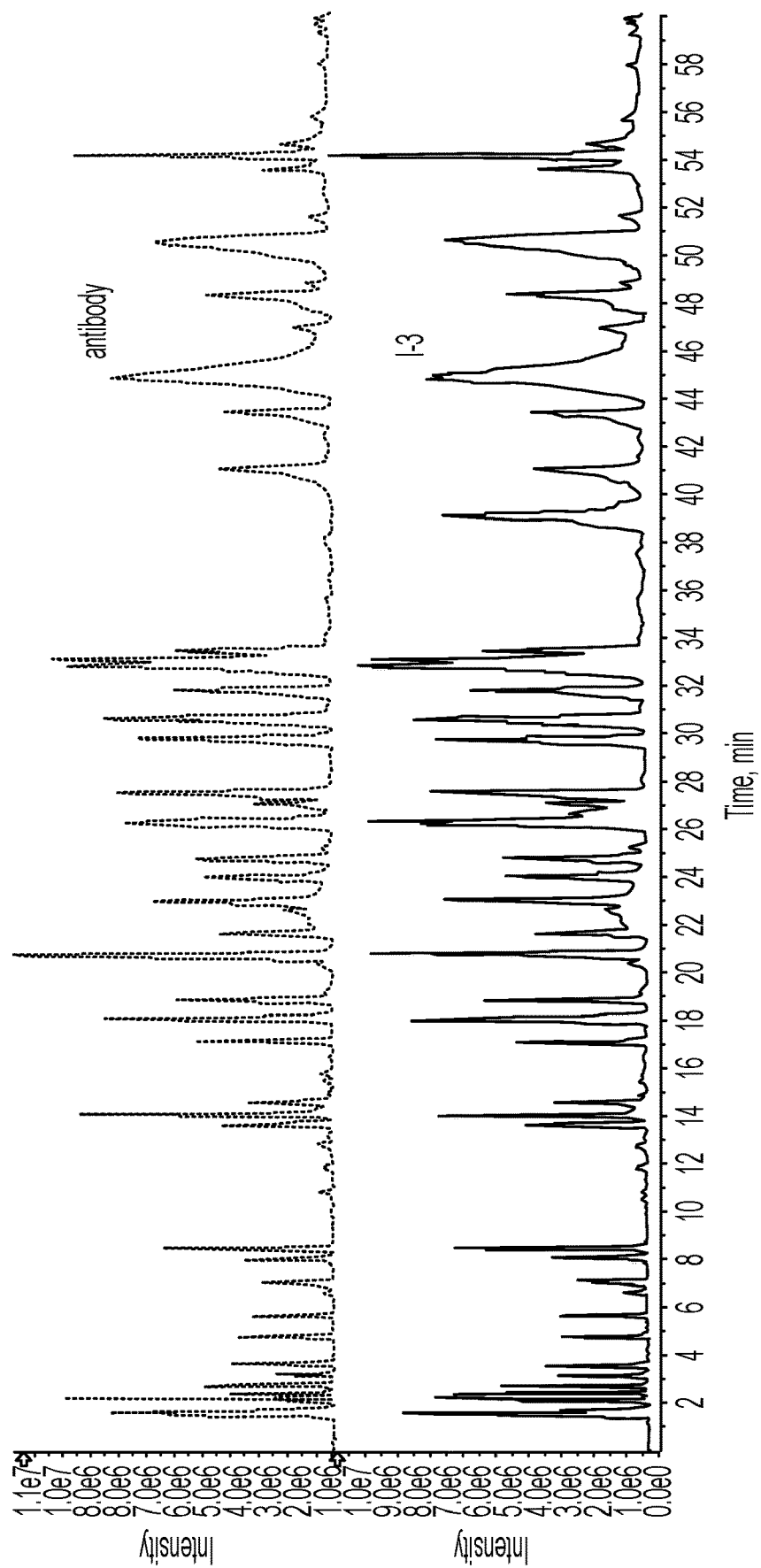
FIG. 12 shows peptide mappings obtained after protease hydrolysis of Antibody-Drug Conjugate I-3 and Trastuzumab under same conditions.

Furthermore, peptide mappings of both Antibody-Drug Conjugate I-3 and Trastuzumab, as shown in FIG. 12, were obtained after digestion under the same conditions.

In the peptide mappings of FIG. 12, the upper curve is the peptide mapping of the antibody at 214 nm, and the lower one is that of Antibody-Drug Conjugate I-3. Comparison shows that Antibody-Drug Conjugate I-3 has only one additional peak at the retention time of 39.0 min. With the reduced chromatograms of the light and heavy chains in FIG. 11, the cytotoxic agents (D) are all conjugated to the lysine residues of the same peptide segment of the light chain in Antibody-Drug Conjugate I-3 obtained in this example, and site specific conjugation assures excellent homogeneity, controllability, and repeatability of the product.

Example 4. In Vivo Activity Test

In this example, the antibody-drug conjugates of Examples 1-3 were evaluated for inhibition of tumor proliferation in mice transplanted with human tumor cells subcutaneously. Specifically, in this example, the antibody-drug conjugates of Examples 1-3 were administered by single intravenous injection in caudal vein to mice transplanted with human gastric cancer cell line NCI-N87, breast cancer cell line BT474, or ovarian cancer cell line SK-OV-3. The change of tumor volume and animal weight were measured for calculation of the efficacy (tumor-inhibitory efficacy) of the antibody-drug conjugates in the tumor-bearing mice.

An appropriate amount of Trastuzumab, T-DM1 (positive control, KADCYLA® (ado-Trastuzumab emtansine), Roche) and the antibody-drug conjugates of the present invention (I-3, I-1 or I-2 prepared in Example 1-3) were weighed, and mother solutions of certain concentrations were prepared using sterile ultrapure water. After gently shaking, the mother solutions were sub-packed and stored at −80° C. Treatment solutions for use were obtained by dilution with normal saline, and a normal saline at the same concentration was used as solvent control.

The tumor-bearing mice (models obtained in 1.2) with tumor volume of 100-200 mm$^3$ were randomly assigned (the number of samples in each group was determined according to sample quantity), 7 mice per group. The dosage was 10 ml/kg. The route of administration was single intravenous injection in caudal vein. After administration, the tumor diameter was measured with vernier caliper twice a week for an observation period of 8 weeks, and the tumor volume was calculated according to the following equation: V=0.5 a$^2$×b, wherein a and b represent the major diameter and the minor diameter of the tumor, respectively. Animal deaths were observed and recorded daily.

The tumor growth inhibition TGI (%) was calculated with the following equation for evaluating the antitumor efficacy of the antibody-drug conjugates:

TGI (%)=[1−($V_{Te}$−$V_{Ts}$)/($V_{Ce}$−$V_{Cs}$)]*100% wherein $V_{Te}$: Average tumor volume of treatment group at the end of observation
$V_{Ts}$: Average tumor volume of treatment group at the administration
$V_{Ce}$: Average tumor volume of control group at the end of observation
$V_{Cs}$: Average tumor volume of control group at the administration
The results are shown in Tables 1-4.

TABLE 1

Breast cancer BT-474 model

| Group | Sample | Dosage (mg/kg) | TGI (%) |
|---|---|---|---|
| 1 | solvent | / | / |
| 2 | T-DM1 | 3 | 54.80% |
| 3 | I-1 | 3 | 104.75% |
| 4 | I-3 | 3 | 107.52% |

The antibody-drug conjugates of the present invention have similar tumor inhibitory efficacy on various breast cancer cell lines.

TABLE 2

Gastric cancer NCI-N87 model

| Group | Sample | Dosage(mg/kg) | initial tumor volume (mm$^3$) | final tumor volume (mm$^3$) |
|---|---|---|---|---|
| 1 | solvent | / | 132.80 | excessive tumor, euthanasia |
| 2 | T-DM1 | 6 | 133.46 | 774.76 |
| 3 | I-2 | 6 | 132.54 | 560.45 |
| 4 | I-3 | 6 | 132.44 | 3.84 |

TABLE 3

Gastric cancer NCI-N87 model

| Group | Sample | Dosage (mg/kg) | TGI (%) |
|---|---|---|---|
| 1 | Solvent | / | / |
| 2 | T-DM1 | 2 | 30.136% |
| 3 | I-1 | 2 | 114.99% |
| 4 | I-3 | 2 | 87.04% |
| 5 | T-DM1 | 3 | 65.28% |
| 6 | I-3 | 3 | 102.72% |

TABLE 4

Ovarian cancer SK-OV-3 model

| Group | Sample | Dosage (mg/kg) | TGI (%) |
|---|---|---|---|
| 1 | Solvent | / | / |
| 2 | T-DM1 | 6 | −11.04% |
| 3 | I-2 | 6 | 54.72% |
| 4 | I-3 | 6 | 72.27% |

As shown in Table 1 to 4, Antibody-Drug Conjugates I-1, I-3 and I-2 of the present invention have apparently superior tumor-inhibitory activity on various tumors, e.g., gastric cancer, ovarian cancer, breast cancer, as compared with T-DM1, and animal deaths indicate their advantageous safety.

Example 5. In Vivo Stability Test

The stability of the antibody-drug conjugates of Examples 1-3 in rats was evaluated in this example. Specifically, in this example, the antibody-drug conjugates of Examples 1-3 were administered to rats by single intravenous injection in caudal vein in a dosage of 2 mg/kg. Blood were regularly collected from jugular vein, and concentrations of the antibody-drug conjugates and the total antibody in the blood were measured by ELISA to calculate the half-lives of the antibody-drug conjugates in rats. The results are shown in Table 5.

TABLE 5

Half-lives of the antibody-drug conjugates

| Antibody-Drug Conjugate | $T_{1/2}$ (h) |
|---|---|
| T-DM1* | 114* |
| I-1 | 247.6 |

TABLE 5-continued

Half-lives of the antibody-drug conjugates

| Antibody-Drug Conjugate | $T_{1/2}$ (h) |
|---|---|
| I-2 | 211.3 |
| I-3 | 259.8 |

*Half-life of T-DM1 in rats was 114 h, according to Bender et al., The AAPS Journal, Vol. 16, No. 5, September 2014.

It can be seen from Table 5 that Antibody-Drug Conjugates I-1, I-2, I-3 of the present invention have longer half-lives, indicating apparently superior stability as compared with T-DM1.

Example 6. Preparation of Lyophilized Powder for Injection of Antibody-Drug Conjugate I-1

Materials in the following table were used to prepare lyophilized powder for injection of Antibody-Drug Conjugate I-1:

| Antibody-Drug Conjugate I-1 | 28 g |
|---|---|
| Ascorbic acid | 20 g |
| Lactic acid | 10 g |
| Polyethylene glycol 4000 | 63 g |
| Water for injection | 2000 ml |

Preparation Method:
1. 20 g ascorbic acid and 10 g lactic acid was added with 1000 ml water for injection and then heated to 50-55° C. and dissolved with stirring. 28 g Antibody-Drug Conjugate was added in the solution, dissolved with stirring, and then stirred for 15 min.
2. 63 g polyethylene glycol 4000 was added with 800 ml water for injection, and stirred for 15 min.
3. After combination of the solutions from 1 and 2, the remaining water for injection was added. 0.15% needle activated carbon was added, the mixture was stirred for 25 min. After carbon remove by filtration, the intermediate product was examined, and if qualified, was filtered for sterilization by 0.22 μm membrane.
4. The filtrate was poured into vials, and freeze-dried to obtain the lyophilized powder for injection. After inspection, the qualified product was packed.

Example 7. Preparation of Lyophilized Powder for Injection of Antibody-Drug Conjugate I-2

Materials in the following table were used to prepare lyophilized powder for injection of Antibody-Drug Conjugate I-2:

| Antibody-Drug Conjugate I-2 | 20 g |
|---|---|
| Sodium succinate | 1.62 g |
| Sucrose | 60 g |
| Tween 20 | 0.2 g |
| Water for injection | 1000 ml |

Preparation Method:
1. 16.2 g sodium succinate, 2 g Tween 20 and 600 g sucrose were added with water for injection to a constant volume of 10 L, and dissolved with stirring. The solution was used as formulation buffer after sterile filtration. An amount of stock solution equivalent to the amount containing 20 g Antibody-Drug Conjugate I-2 was ultrafiltrated with the formulation buffer for exchanging with the latter, and then concentrated to 1000 ml.
2. The solution from 1 was filtered for sterilization by 0.22 μm membrane.
3. The filtrate was poured into vials, and freeze-dried to obtain the lyophilized powder for injection. After inspection, the qualified product was packed.

Example 8. Preparation of Lyophilized Powder for Injection of Antibody-Drug Conjugate I-3

Materials in the following table were used to prepare lyophilized powder for injection of Antibody-Drug Conjugate I-3:

| Antibody-Drug Conjugate I-3 | 20 g |
|---|---|
| L-histidine | 0.32 g |
| L-histidine hydrochloride | 0.495 g |
| Trehalose dihydrate | 20 g |
| Tween 20 | 0.09 g |
| Water for injection | 1000 ml |

Preparation Method:
1. 3.2 g L-histidine, 4.95 g L-histidine hydrochloride, 200 g Trehalose dihydrate and 0.9 g Tween 20 were added with water for injection to a constant volume of 10 L, and dissolved with stirring. The solution was used as formulation buffer after sterile filtration. An amount of stock solution equivalent to the amount containing 20 g Antibody-Drug Conjugate I-3 was ultrafiltrated with the formulation buffer for exchanging with the latter, and then concentrated to 1000 ml.
2. The solution from 1 was filtered for sterilization by 0.22 μm membrane.
3. The filtrate was poured into vials, and freeze-dried to obtain the lyophilized powder for injection. After inspection, the qualified product was packed.

Although the present invention has been illustrated by way of the specific examples above, it should not be interpreted as being limited to the examples. The present invention contemplates the general aspects disclosed above, and those skilled in the art can make various modifications or changes to the various details of the present invention without departing from the spirit and scope of the present invention. Therefore, the specification is for illustrative purpose only, not for any restrictions.

What is claimed is:

1. A preparation method of an antibody-drug conjugate represented by Formula (I), or a pharmaceutically acceptable salt or stereoisomer thereof, or a solvate of the foregoing,

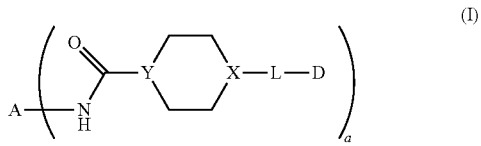

wherein:
A is an anti-ErbB2 antibody, wherein the anti-ErbB2 antibody is Trastuzumab;
X is N;
Y is N or $CR^1$, and $R^1$ is H or $C_1$-$C_{10}$ alkyl;
L is

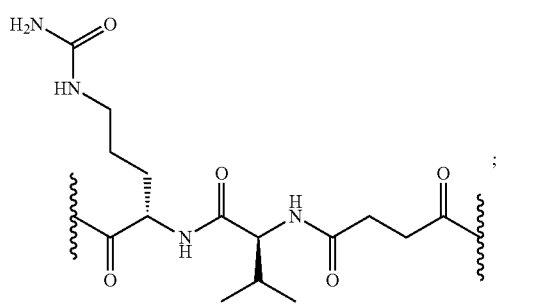 [SMILES: *C(=O)CCC(=O)N[C@H](C(=O)N[C@@H](CCCNC(N)=O)C(*)=O)C(C)C]

D is a cytotoxic agent group of Formula (D1) or a stereoisomer thereof,

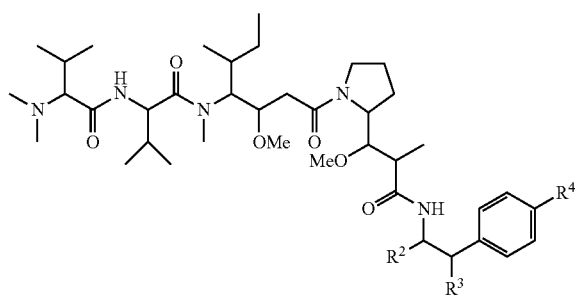

wherein $R^2$ is —$CH_2N_3$, $R^3$ is selected from the group consisting of H and —OH, and $R^4$ is selected from the group consisting of H, —$NH_2$, Cl, Br, I and —$OS(O)_2$ $R^6$, wherein $R^6$ is H, $C_1$-$C_8$ alkyl, $C_3$-$C_8$ cycloalkyl or $C_6$-$C_{14}$ aryl, and the alkyl, cycloalkyl and aryl are each optionally substituted with one or more halogen substituents;
a is an integer selected from the group consisting of 2-10; and all the cytotoxic agent groups are conjugated to the lysine residues of the same peptide segment of the light chain of the antibody;

the method comprising the steps of:

(1) preparing a compound of Formula (I-A):

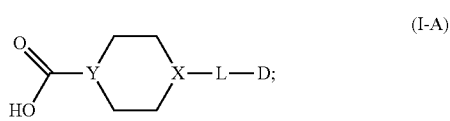

(2) obtaining a compound of Formula (I-B) by reacting the compound of Formula (I-A) with pentafluorophenol using 1-ethyl-3-(3-dimethylaminopropyl)carbodiimide, N-hydroxysuccinimide and/or dichloromethane

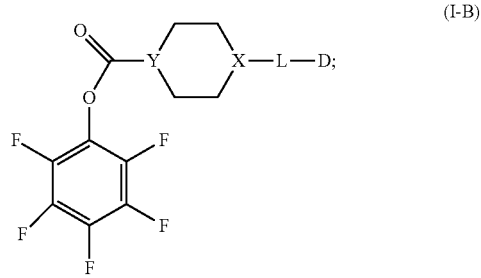

(3) obtaining a mixture of a variety of antibody-drug conjugates having different a values by conjugating the compound of Formula (I-B) from step (2) with the anti-ErbB2 antibody; and (4) obtaining the antibody-drug conjugate represented by Formula (I) by purifying the mixture from step (3) with hydrophobic interaction chromatography (HIC) method, said method utilizing a stationary phase that comprises a phenyl resin;

wherein a mobile phase A of the HIC method comprises ammonia sulfate and disodium hydrogen phosphate; and a mobile phase B of the HIC method comprises disodium hydrogen phosphate and isopropanol.

2. The preparation method according to claim 1, wherein Y is $CR^1$.

3. The preparation method according to claim 1, wherein $R^1$ is H.

4. The preparation method according to claim 1, wherein a is 2, 3 or 4.

5. The preparation method according to claim 1, wherein the antibody-drug conjugate is represented by Formula (I-1):

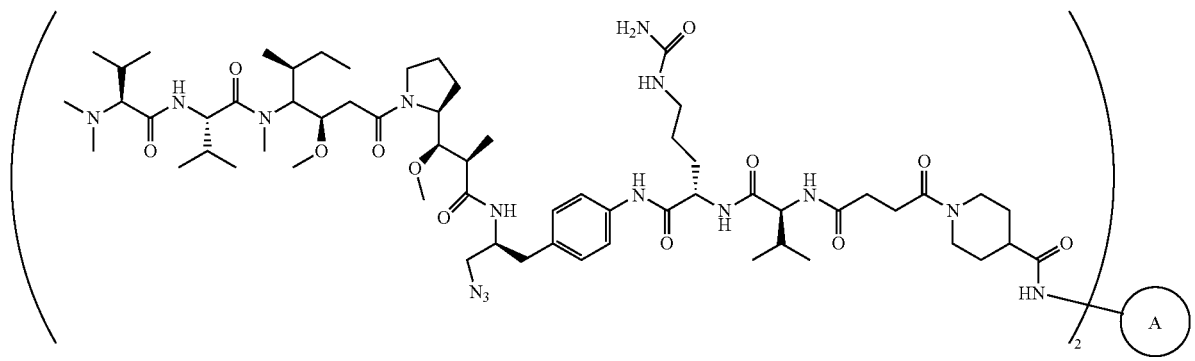
(I-1)
wherein A is Trastuzumab.
6. The preparation method according to claim 1, wherein $R^6$ is H, $C_1$-$C_8$ alkyl, $C_3$-$C_8$ cycloalkyl or $C_6$-$C_{14}$ aryl, and the alkyl, cycloalkyl and aryl are each optionally substituted with 1, 2, 3, 4 or 5 halogen substituents.
7. The preparation method according to claim 1, wherein the one or more halogen substituents are one or more F substituents.
* * * * *